(12) United States Patent
Knapp et al.

(10) Patent No.: US 10,851,303 B2
(45) Date of Patent: Dec. 1, 2020

(54) AZEOTROPIC COMPOSITIONS COMPRISING HYDROGEN FLUORIDE AND FLUOROCARBONS

(71) Applicant: The Chemours Company FC, LLC, Wilmington, DE (US)

(72) Inventors: Jeffrey Knapp, Wilmington, DE (US); Sheng Peng, Hockessin, DE (US); Olagappan Muthu, Wilmington, DE (US)

(73) Assignee: THE CHEMOURS COMPANY FC, LLC, Wilmington, DE (US)

(*) Notice: Subject to any disclaimer, the term of this patent is extended or adjusted under 35 U.S.C. 154(b) by 0 days.

(21) Appl. No.: 16/047,422

(22) Filed: Jul. 27, 2018

(65) Prior Publication Data

US 2019/0040321 A1 Feb. 7, 2019

Related U.S. Application Data

(60) Provisional application No. 62/537,781, filed on Jul. 27, 2017.

(51) Int. Cl.
C09K 21/08 (2006.01)
C09K 3/30 (2006.01)
(Continued)

(52) U.S. Cl.
CPC ............ *C09K 21/08* (2013.01); *C01B 7/191* (2013.01); *C07C 19/10* (2013.01); *C07C 19/12* (2013.01); *C07C 21/18* (2013.01); *C07C 23/06* (2013.01); *C08J 9/144* (2013.01); *C08J 9/146* (2013.01); *C09K 3/14* (2013.01); *C09K 3/30* (2013.01); *C09K 5/044* (2013.01); *C09K 5/045* (2013.01); *C11D 3/04* (2013.01); *C11D 3/245* (2013.01); *H01B 3/56* (2013.01); *C07C 2601/06* (2017.05); *C08J 2203/162* (2013.01); *C08J 2300/00* (2013.01); *C09K 2205/126* (2013.01); *C09K 2205/32* (2013.01)

(58) Field of Classification Search
None
See application file for complete search history.

(56) References Cited

U.S. PATENT DOCUMENTS 5,146,019 A 9/1992 Bielefeldt et al.
2002/0137645 A1 9/2002 Pham et al.
(Continued)

FOREIGN PATENT DOCUMENTS

EP 0 581 961 2/1994
EP 2 254 851 12/2010
WO WO 2009/105517 8/2009

OTHER PUBLICATIONS

International Search Report and Written Opinion in Application No. PCT/US2018/044077, dated Sep. 19, 2018, 14 pages.
(Continued)

*Primary Examiner* — William D Young

(57) ABSTRACT

The present application discloses compositions comprising hydrogen fluoride and fluorinated compounds (e.g., hydrochlorofluorocarbons), wherein the fluorinated compound is present in the composition in an amount effective to form an azeotrope composition or azeotrope-like composition with the hydrogen fluoride.

5 Claims, 1 Drawing Sheet

(51) Int. Cl.
*C09K 5/04* (2006.01)
*H01B 3/56* (2006.01)
*C07C 21/18* (2006.01)
*C07C 23/06* (2006.01)
*C01B 7/19* (2006.01)
*C07C 19/10* (2006.01)
*C07C 19/12* (2006.01)
*C08J 9/14* (2006.01)
*C09K 3/14* (2006.01)
*C11D 3/04* (2006.01)
*C11D 3/24* (2006.01)

(56) References Cited

U.S. PATENT DOCUMENTS

| | | |
|---|---|---|
| 2006/0106263 A1 | 5/2006 | Miller et al. |
| 2007/0100174 A1 | 5/2007 | Miller et al. |
| 2008/0051612 A1 | 2/2008 | Knapp et al. |
| 2011/0101264 A1 | 5/2011 | Knapp |
| 2012/0215039 A1 | 8/2012 | Hulse et al. |
| 2012/0305382 A1* | 12/2012 | Knapp .................... C07C 21/18 203/67 |

OTHER PUBLICATIONS

Zhang et al. "Synthesis of Z-1,1,1,4,4,4-hexafluoro-2-butene from Hexachlorobutadiene," Journal of Fluorine Chemistry, 2016, 191: 77-83.

* cited by examiner

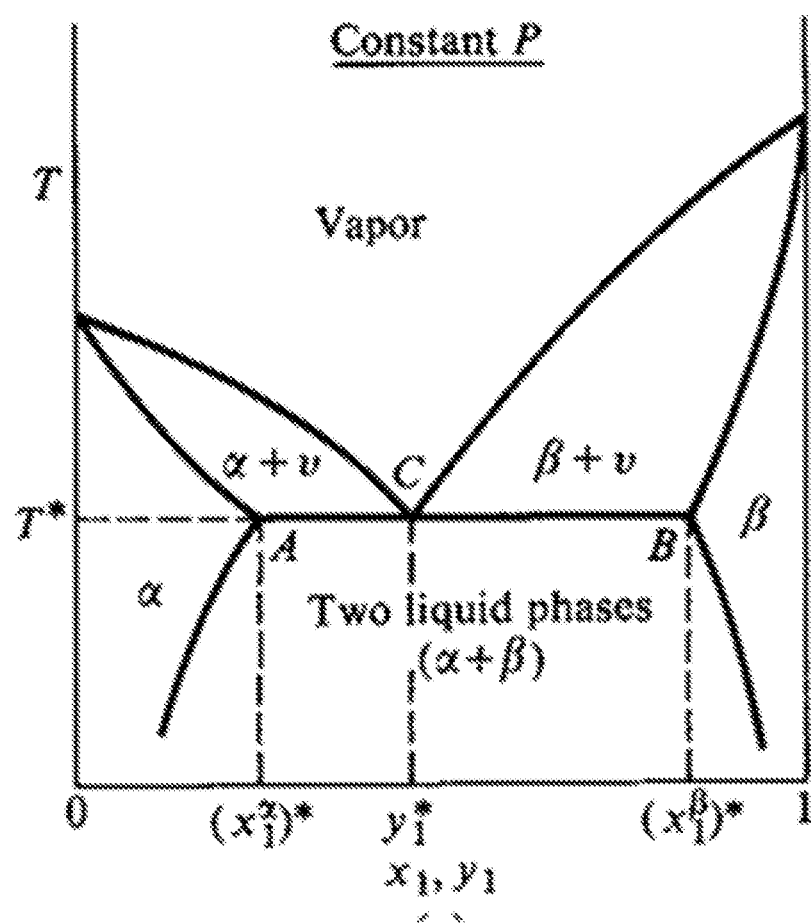

AZEOTROPIC COMPOSITIONS COMPRISING HYDROGEN FLUORIDE AND FLUOROCARBONS

CROSS-REFERENCE TO RELATED APPLICATIONS

This application claims the benefit of U.S. Provisional Application Ser. No. 62/537,781, filed Jul. 27, 2017, the disclosure of which is incorporated herein by reference in its entirety.

TECHNICAL FIELD

This invention relates to compositions comprising hydrogen fluoride and hydrochlorofluorocarbon (HCFC) or chlorofluorocarbon (CFC) compounds, wherein the hydrochlorofluorocarbon or chlorofluorocarbon is present in the composition in an amount effective to form an azeotrope composition or azeotrope-like composition with the hydrogen fluoride.

BACKGROUND

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs).

SUMMARY

The present application provides, inter alia, a composition comprising:
  i) hydrogen fluoride; and
  ii) a compound of Formula I:

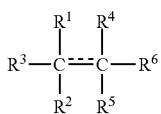

wherein constituent members are defined herein, and wherein the compound of Formula I is present in an amount effective to form an azeotrope composition or an azeotrope-like composition with the hydrogen fluoride.

The present application further comprises a composition, comprising:
  i) hydrogen fluoride; and
  ii) a compound selected from the group consisting of:
    2,3-dichlorohexafluoro-2-butene;
    2-chloro-1,1,1,4,4,4-hexafluoro-2-butene;
    2,3-dichloro-1,1,1,4,4,4-hexafluorobutane;
    2-chloro-1,1,1,3,4,4,4-heptafluorobut-2-ene;
    1,1,1,2,4,4,4-heptafluorobut-2-ene;
    2-chloro-1,1,1,2,4,4,4-heptafluorobutane;
    1,2-dichloro-1,1,4,4,4-pentafluorobut-2-ene;
    1,2-dichloro-1,1,2,2-tetrafluoroethane;
    2-chloro-1,1,1,3,4,4,4-heptafluorobutane;
    2-chloro-1,1,1,3,3-pentafluoropropane;
    1,2-dichloro-1,1,2-trifluoroethane;
    2,2-dichloro-1,1,1,4,4,4-hexafluorobutane;
    1,2-dichloro-1,1,2,4,4,4-hexafluorobutane;
    1,2-dichloro-3,3,4,4,4-pentafluorobut-1-ene;
    2,3-dichloro-1,1,1,3-tetrafluoropropane;
    1,2,3-trichloro-1,1,4,4,4-pentafluorobutane;
    1,2,2-trichloro-1,1-difluoroethane;
    1,1,2,2-tetrachloro-1,2-difluoroethane;
    1,1,1,2-tetrachloro-2,2-difluoroethane;
    1,2-dichloro-3,3,4,4-tetrafluorocyclobut-1-ene; and
    1,1,2,3-tetrachloro-4,4,4-trifluorobut-1-ene;
  wherein the compound is present in an amount effective to form an azeotrope composition or an azeotrope-like composition with the hydrogen fluoride.

The present application further comprises a composition, comprising:
  i) hydrogen fluoride; and
  ii) a compound selected from the group consisting of:
    2,3-dichlorohexafluoro-2-butene;
    (E)-2,3-dichlorohexafluoro-2-butene;
    (Z)-2,3-dichlorohexafluoro-2-butene;
    (E)-2-chloro-1,1,1,4,4,4-hexafluoro-2-butene;
    (Z)-2-chloro-1,1,1,4,4,4-hexafluoro-2-butene;
    (d1)-2,3-dichloro-1,1,1,4,4,4-hexafluorobutane;
    meso-2,3-dichloro-1,1,1,4,4,4-hexafluorobutane;
    2-chloro-1,1,1,3,4,4,4-heptafluorobut-2-ene;
    1,1,1,2,4,4,4-heptafluorobut-2-ene;
    2-chloro-1,1,1,2,4,4,4-heptafluorobutane;
    (Z)-1,2-dichloro-1,1,4,4,4-pentafluorobut-2-ene;
    1,2-dichloro-1,1,2,2-tetrafluoroethane;
    2-chloro-1,1,1,3,4,4,4-heptafluorobutane;
    2-chloro-1,1,1,3,3-pentafluoropropane;
    1,2-dichloro-1,1,2-trifluoroethane;
    2,2-dichloro-1,1,1,4,4,4-hexafluorobutane;
    1,2-dichloro-1,1,2,4,4,4-hexafluorobutane;
    1,2-dichloro-3,3,4,4,4-pentafluorobut-1-ene;
    2,3-dichloro-1,1,1,3-tetrafluoropropane;
    1,2,3-trichloro-1,1,4,4,4-pentafluorobutane;
    1,2,2-trichloro-1,1-difluoroethane;
    1,1,2,2-tetrachloro-1,2-difluoroethane;
    1,1,1,2-tetrachloro-2,2-difluoroethane;
    1,2-dichloro-3,3,4,4-tetrafluorocyclobut-1-ene; and
    1,1,2,3-tetrachloro-4,4,4-trifluorobut-1-ene;
  wherein the compound is present in an amount effective to form an azeotrope composition or an azeotrope-like composition with the hydrogen fluoride.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

BRIEF DESCRIPTION OF THE DRAWINGS

FIG. 1 shows an exemplary vapor-liquid equilibrium plot representative of the properties of heterogeneous azeotropes.

DETAILED DESCRIPTION

The HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future. Thus, there is a need for compositions that do not contribute to the destruction of stratospheric ozone and also have low global warming potentials (GWPs). Certain hydrofluoroolefins, such as 1,1,1,4,4,4-hexafluoro-2-butene (CF$_3$CH=CHCF$_3$, HFO-1336mzz), meets both goals. For example, (Z)-HFO-1336mzz (i.e., (Z)-1,1,1,4,4,4-hexafluoro-2-butene) is useful in many applications (e.g., a foam expansion agent or refrigerant) due to its low GWP, non-flammability, high efficiency, and thermal stability. (Z)-1,1,1,4,4,4-hexafluoro-2-butene may be prepared, for example, via a three-step preparation from hexachlorobutadiene, as shown below in Schemes 1-2.

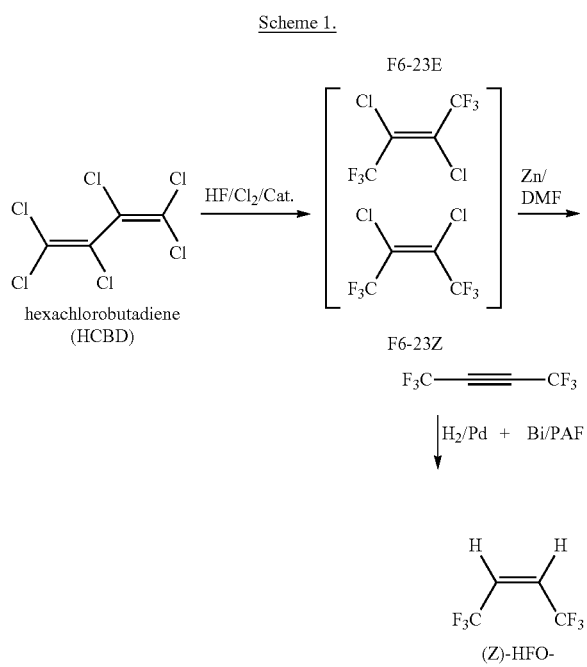

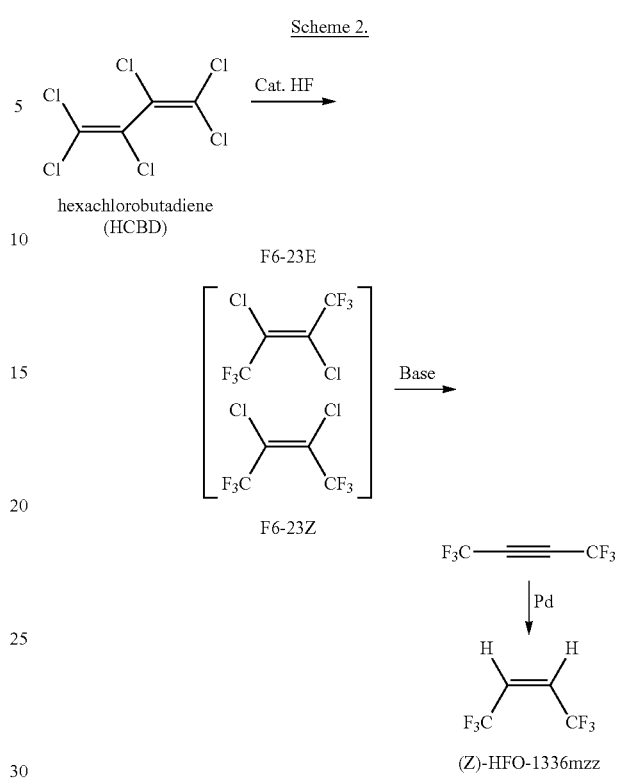

Numerous by-products are formed during liquid phase or gas phase preparations of (Z)-1,1,1,4,4,4-hexafluoro-2-butene, for example, as shown below in Scheme 3. These products include, but are not limited to, (E)-1326mxz, (Z)-1326mxz, 336mdd-d1, 336mdd-meso, (E)-1316mxx, (Z)-1316mxx, and other fluorinated compounds described herein which are formed in the preparation of (Z)-1,1,1,4,4,4-hexafluoro-2-butene or 1,1,1,4,4,4-hexafluorobut-2-yne (i.e., perfluorobut-2-yne) which is a key intermediate in the 3-step preparation of (Z)-1,1,1,4,4,4-hexafluoro-2-butene shown above in Scheme 1. The formation of azeotropic or azeotrope-like compositions comprising hydrogen fluoride and the compounds described herein (e.g., compounds of Formula I) allow said compounds to be removed more easily and at lower temperatures from other higher boiling by-products formed in the synthesis of (Z)-1,1,1,4,4,4-hexafluoro-2-butene, allowing for improved purification of the desired products at lower energy and reduced cost. Additionally, said azeotropic compositions can be used in azeotropic distillations to remove hydrogen fluoride from higher boiling compounds that also form azeotropes with hydrogen fluoride.

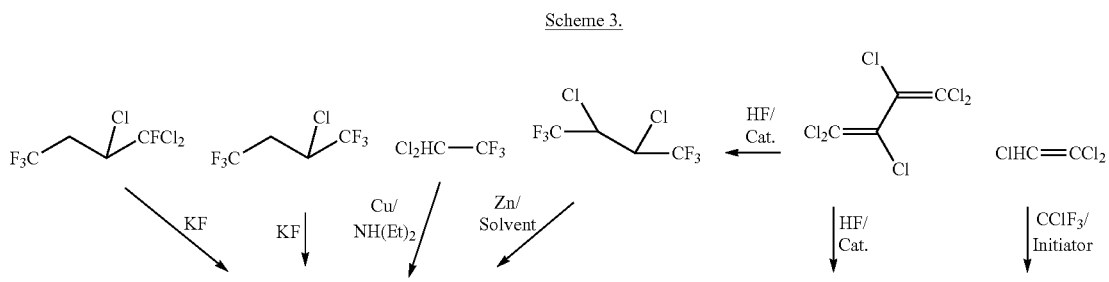

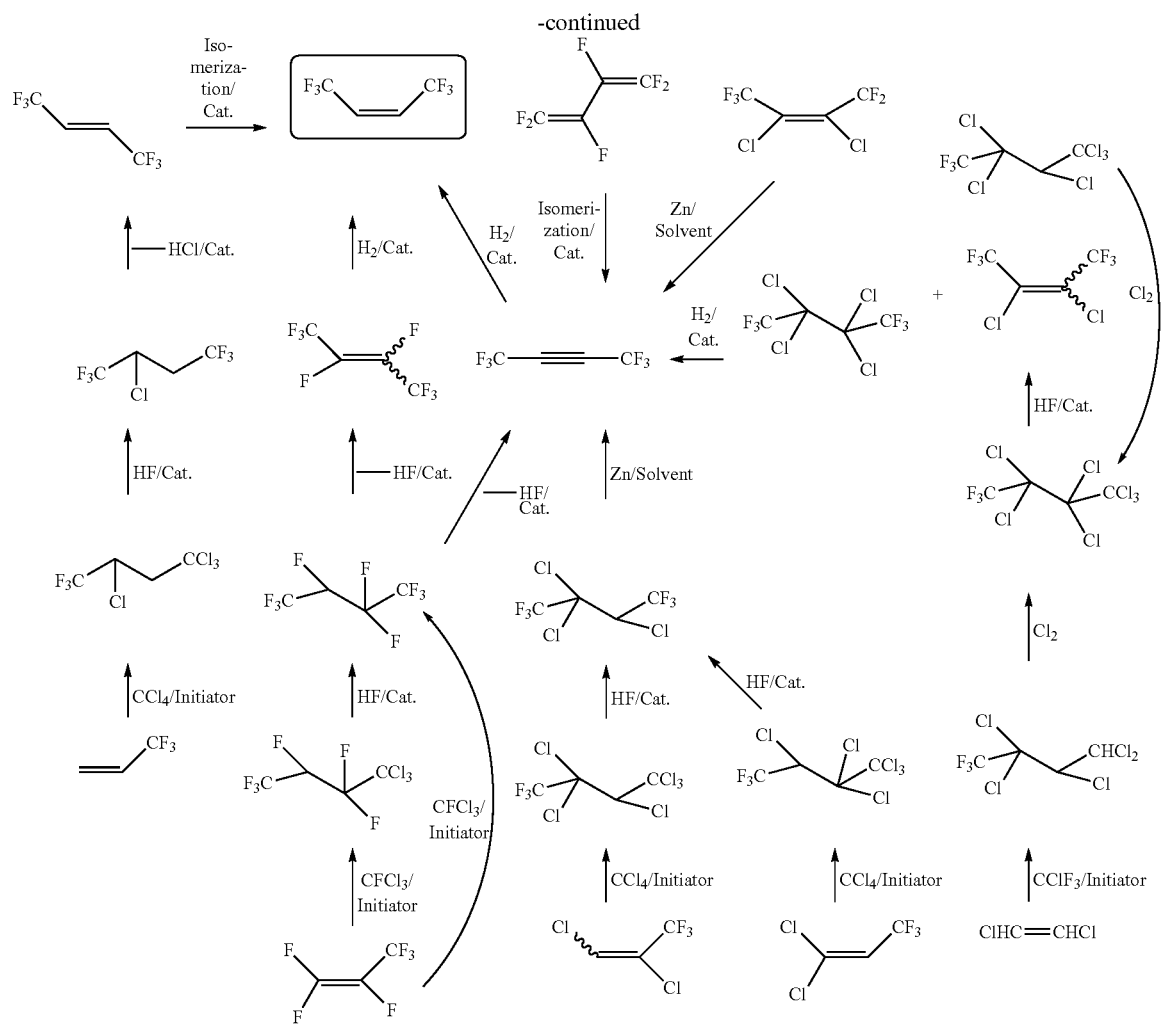

-continued

Definitions and Abbreviations

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

As used herein, the term "about" is meant to account for variations due to experimental error (e.g., plus or minus approximately 10% of the indicated value). All measurements reported herein are understood to be modified by the term "about", whether or not the term is explicitly used, unless explicitly stated otherwise.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

Global warming potential (GWP) is an index for estimating relative global warming contribution due to atmospheric emission of a kilogram of a particular greenhouse gas compared to emission of a kilogram of carbon dioxide. GWP can be calculated for different time horizons showing the effect of atmospheric lifetime for a given gas. The GWP for the 100-year time horizon is commonly the value referenced.

As used herein the term "Ozone depletion potential" (ODP) is defined in "The Scientific Assessment of Ozone Depletion, 2002, A report of the World Meteorological Association's Global Ozone Research and Monitoring Project," section 1.4.4, pages 1.28 to 1.31 (see first paragraph of this section). ODP represents the extent of ozone depletion in the stratosphere expected from a compound on a mass-for-mass basis relative to fluorotrichloromethane (CFC-11).

As recognized in the art, an azeotropic composition is an admixture of two or more different components which, when in liquid form and (1a) under a given constant pressure, will boil at a substantially constant temperature, which temperature may be higher or lower than the boiling temperatures of the individual components, or (1b) at a given constant temperature, will boil at a substantially constant pressure, which pressure may be higher or lower than the boiling pressure of the individual components, and (2) will boil at substantially constant composition, which phase compositions, while constant, are not necessarily equal. (See, e.g., M. F. Doherty and M. F. Malone, Conceptual Design of Distillation Systems, McGraw-Hill (New York), 2001, 185).

A homogeneous azeotrope, in which a single vapor phase is in equilibrium with a single liquid phase, has, in addition to properties (1a), (1b), and (2) above, the composition of each component is the same in each of the coexisting equilibrium phases. The general term "azeotrope" is a commonly used alternative name for a homogeneous azeotrope.

A heterogeneous azeotrope, in which a single vapor phase is in equilibrium with two liquid phases, has properties (1a), (1b), and (2) as described above where, while constant, the three coexisting equilibrium phases each have different compositions (See e.g., M. F. Doherty and M. F. Malone, Conceptual Design of Distillation Systems, McGraw-Hill (New York), 2001, 352). At the heterogeneous azeotrope, the composition of the overall liquid phase, (i.e., the liquid phase composition obtained by combining the two equilibrium liquid phases), is identical to the composition of the equilibrium vapor phase.

The properties of heterogeneous azeotropes are described, for example, in FIG. 1. As shown in FIG. 1, temperature T* is the minimum temperature at which both vapor and liquid phases occur. Below T*, depending on composition, liquid phase α, liquid phase β, or both α and β will exist. When the liquid composition lies within the (α+β) region, it splits into two separate liquid phases whose compositions are defined by the intersection of the solid lines starting at points A and B and continuing toward the bottom of FIG. 1 and a horizontal line at the specified temperature (FIG. 1). Above T*, in regions (α+v) and (β+v), a single liquid phase is in equilibrium with a vapor phase whose compositions are indicated by the intersection of the solid lines bounding region (α+v) or (β+v), depending on the mixture composition, and a horizontal line at the specified temperature. At temperature T*, three phases of different compositions, denoted by A, B, and C in FIG. 1, are in equilibrium with each other. Any mixture with a liquid phase composition between $(x_1^\alpha)^*$ and $(x_1^\beta)^*$ as shown in FIG. 1 will (I) split into two liquid phases with compositions equal to $(x_1^\alpha)^*$ and $(x_1^\beta)^*$, (II) be in equilibrium with a vapor phase of composition $y_1^*$, and (III) boil at the same temperature T*. Points A, B, and C and temperature T* of FIG. 1 constitute the three equilibrium phases of a heterogeneous azeotrope. At the azeotropic composition, the overall liquid phase composition equals $y_1^*$.

As used herein, an "azeotrope-like" composition refers to a composition that behaves like an azeotropic composition (i.e., has constant boiling characteristics or a tendency not to fractionate upon boiling or evaporation). Hence, during boiling or evaporation, the vapor and liquid compositions, if they change at all, change only to a minimal or negligible extent. In contrast, the vapor and liquid compositions of non-azeotrope-like compositions change to a substantial degree during boiling or evaporation.

As used herein, the terms "azeotrope-like" or "azeotrope-like behavior" refer to compositions that exhibit dew point pressure and bubble point pressure with virtually no pressure differential. In some embodiments, the difference in the dew point pressure and bubble point pressure at a given temperature is 3% or less. In some embodiments, the difference in the bubble point and dew point pressures is 5% or less.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl" refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group has 1 to 6, 1 to 4, 1 to 3, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "halo" refers to fluoro, chloro, bromo, or iodo. In some embodiments, the halo is chloro or fluoro.

As used herein, the term "$C_{n-m}$ haloalkyl" refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only (i.e., a partially fluorinated alkyl or a perfluorinated alkyl). In some embodiments, the haloalkyl group has 1 to 6, 1 to 4, 1 to 3, or 1 to 2 carbon atoms.

As used herein, the term "$C_{n-m}$ haloalkenyl" refers to an alkenyl group having from 1 halogen atom to 2s-1 halogen atoms, which may be the same or different, where "s" is the number of carbon atoms in the alkenyl group. In some embodiments, the haloalkenyl group is chlorinated only (i.e., a partially chlorinated alkenyl or a perchlorinated alkenyl). In some embodiments, the haloalkenyl group has 2 to 6, 2 to 4, or 2 to 3 carbon atoms.

Chemicals, Abbreviations, and Acronyms

112: 1,1,2,2-tetrachloro-1,2-difluoroethane
112a: 1,1,1-tetrachloro-2,2-difluoroethane
114: 1,2-dichloro-1,1,2,2-tetrafluoroethane
122: 1,2,2-trichloro-1,1-difluoroethane
123a: 1,2-dichloro-1,1,2-trifluoroethane
234da: 2,3-dichloro-1,1,1,3-tetrafluoropropane
235da: 2-chloro-1,1,1,3,3-pentafluoropropane
3351dd: 1,2,3-trichloro-1,1,4,4,4-pentafluorobutane
3361bf: 1,2-dichloro-1,1,2,4,4,4-hexafluorobutane
336maf: 2,2-dichloro-1,1,1,4,4,4-hexafluorobutane
336mdd: 2,3-dichloro-1,1,1,4,4,4-hexafluorobutane (mixture of isomers)

336mdd-d1: 2,3-dichloro-1,1,1,4,4,4-hexafluorobutane (d1 isomer)
336mdd-meso: meso-2,3-dichloro-1,1,1,4,4,4-hexafluorobutane
337mbf: 2-chloro-1,1,1,2,4,4,4-heptafluorobutane (mixture of isomers)
337mde: 2-chloro-1,1,1,3,4,4,4-heptafluorobutane
1316mxx: 2,3-dichlorohexafluoro-2-butene (mixture of isomers)
E-1316mxx or E-CFC-1316mxx: (E)-2,3-dichlorohexafluoro-2-butene
Z-1316mxx or Z-CFC-1316mxx: (Z)-2,3-dichlorohexafluoro-2-butene
1314: 1,2-dichloro-3,3,4,4-tetrafluorocyclobut-1-ene
1317mx: 2-chloro-1,1,1,3,4,4,4-heptafluorobut-2-ene (mixture of isomers)
E-1317mx: (E)-2-chloro-1,1,1,3,4,4,4-heptafluorobut-2-ene
Z-1317mx: (Z)-2-chloro-1,1,1,3,4,4,4-heptafluorobut-2-ene
1323azd: 1,1,2,3-tetrachloro-4,4,4-trifluorobut-1-ene
1325lxz: 1,2-dichloro-1,1,4,4,4-pentafluorobut-2-ene (mixture of isomers)
E-1325lxz: (E)-1,2-dichloro-1,1,4,4,4-pentafluorobut-2-ene
Z-1325lxz: (Z)-1,2-dichloro-1,1,4,4,4-pentafluorobut-2-ene
1325dx: 1,2-dichloro-3,3,4,4,4-pentafluorobut-1-ene
1326mxz: 2-chloro-1,1,1,4,4,4-hexafluoro-2-butene (mixture of isomers)
E-1326mxz: (E)-2-chloro-1,1,1,4,4,4-hexafluoro-2-butene
Z-1326mxz: (Z)-2-chloro-1,1,1,4,4,4-hexafluoro-2-butene
1327mz: 1,1,1,2,4,4,4-heptafluorobut-2-ene (mixture of isomers)
E-1327mz: (E)-1,1,1,2,4,4,4-heptafluorobut-2-ene
Z-1327mz: (Z)-1,1,1,2,4,4,4-heptafluorobut-2-ene
CFC: chlorofluorocarbon
HCBD: hexachlorobutadiene
HCFC: hydrochlorofluorocarbon
HFO-1336mzz(Z) or 1336mzz-Z: (Z)-1,1,1,4,4,4-hexafluoro-2-butene
VLE: vapor-liquid equilibrium
NRTL: Non-Random, Two-Liquid Compositions The present application provides a composition comprising:
i) hydrogen fluoride; and
ii) a compound of Formula I:

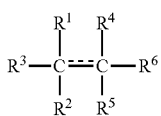

wherein ===== refers to a single bond or a double bond;
$R^1$ is selected from the group consisting of H, halo, and $C_{1-3}$ haloalkyl;
$R^2$ is selected from the group consisting of halo and $C_{1-3}$ haloalkyl;
$R^3$ is selected from the group consisting of $C_{1-3}$ haloalkyl; or alternatively, $R^3$ is absent when ===== forms a double bond;
$R^4$ is selected from the group consisting of halo and $C_{1-3}$ haloalkyl;
$R^5$ is selected from the group consisting of H, $C_{1-3}$ haloalkyl and $C_{1-3}$ haloalkenyl,
wherein $R^5$ is not H when ===== forms a double bond;
$R^6$ is H;
or alternatively, $R^6$ is absent when ===== forms a double bond;
wherein when ===== forms a single bond and $R^5$ is H, then $R^1$ is chloro, $R^2$ is fluoro, and $R^3$ and $R^4$ are each trifluoromethyl; and
wherein the compound of Formula I is present in an amount effective to form an azeotrope composition or an azeotrope-like composition with the hydrogen fluoride.

In some embodiments:
===== refers to a single bond or a double bond;
$R^1$ is selected from the group consisting of H, halo, and $C_{1-3}$ haloalkyl;
$R^2$ is selected from the group consisting of halo and $C_{1-3}$ haloalkyl;
$R^3$ is selected from the group consisting of $C_{1-3}$ haloalkyl; or alternatively, $R^3$ is absent when ===== forms a double bond;
$R^4$ is selected from the group consisting of halo and $C_{1-3}$ haloalkyl;
$R^5$ is selected from the group consisting of $C_{1-3}$ haloalkyl and $C_{1-3}$ haloalkenyl;
$R^6$ is H;
or alternatively, $R^6$ is absent when ===== forms a double bond; and
wherein the compound of Formula I is present in an amount effective to form an azeotrope composition or an azeotrope-like composition with the hydrogen fluoride.

The compounds provided herein (e.g., compound of Formula I) include stereoisomers of the compounds. All stereoisomers, such as enantiomers and diastereomers, are intended unless otherwise indicated. In some embodiments, the compound of Formula I is the (E)-isomer. In some embodiments, the compound of Formula I is the (Z)-isomer. In some embodiments, the compound of Formula I is a mixture of (E)- and (Z)-isomers.

In some embodiments, the compositions provided herein are azeotropic compositions or azeotrope-like compositions. In some embodiments, the compositions provided herein are homogeneous azeotropic or homogeneous azeotrope-like compositions. In some embodiments, the compositions provided herein are heterogeneous azeotropic compositions or heterogeneous azeotrope-like compositions. In some embodiments, the compositions provided herein are homogeneous azeotropic compositions. In some embodiments, the compositions provided herein are heterogeneous azeotropic compositions.

It is understood that the effective amount of each component of the compositions provided herein (e.g., hydrogen fluoride and a compound of Formula I), may vary depending on the pressure applied to the composition so long as the azeotropic or azeotrope-like compositions continue to exist at the different pressures, but with possible different boiling points. Therefore, effective amount includes the amounts, such as may be expressed in weight or mole percentages, of each component of the compositions of the instant invention which form azeotropic or azeotrope-like compositions at temperatures or pressures other than as described herein.

In some embodiments, $R^1$ is H or halo. In some embodiments, $R^1$ is selected from the group consisting of H, chloro, and fluoro.

In some embodiments, $R^2$ is selected from the group consisting of chloro, fluoro, and $C_{1-3}$ fluoroalkyl. In some embodiments, $R^2$ is selected from the group consisting of chloro and $C_{1-3}$ fluoroalkyl. In some embodiments, $R^2$ is selected from the group consisting of chloro and trifluoromethyl.

In some embodiments, $R^4$ is halo. In some embodiments, $R^4$ is chloro or fluoro.

In some embodiments, $R^5$ is selected from the group consisting of H, $C_{1-3}$ fluoroalkyl, and $C_{1-3}$ chloroalkenyl. In some embodiments, $R^5$ is $C_{1-3}$ fluoroalkyl or $C_{1-3}$ chloroalkenyl. In some embodiments, $R^5$ is trifluoromethyl or 1,2,2-trichloroethenyl. In some embodiments, $R^5$ is H.

In some embodiments, ===== is a single bond. In some embodiments, $R^3$ is H. In some embodiments, $R^6$ is H. In some embodiments, $R^3$ and $R^6$ are each H. In some embodiments, ===== is a double bond.

In some embodiments, the compound of Formula I is selected from the group consisting of:
2,3-dichlorohexafluoro-2-butene;
2-chloro-1,1,1,4,4,4-hexafluoro-2-butene;
2,3-dichloro-1,1,1,4,4,4-hexafluorobutane;
2-chloro-1,1,1,3,4,4,4-heptafluorobut-2-ene;
2-chloro-1,1,1,2,4,4,4-heptafluorobutane;
1,2-dichloro-1,1,4,4,4-pentafluorobut-2-ene;
1,1,1,2,4,4,4-heptafluorobut-2-ene;
wherein the compound of Formula I is present in an amount effective to form an azeotrope or an azeotrope-like composition with the hydrogen fluoride.

In some embodiments, the compound of Formula I is selected from the group consisting of:
2,3-dichlorohexafluoro-2-butene (i.e., a mixture of (E)-2,3-dichlorohexafluoro-2-butene and (Z)-2,3-dichlorohexafluoro-2-butene);
(E)-2,3-dichlorohexafluoro-2-butene;
(Z)-2,3-dichlorohexafluoro-2-butene;
2-chloro-1,1,1,4,4,4-hexafluoro-2-butene (i.e., a mixture of (E)-2-chloro-1,1,1,4,4,4-hexafluoro-2-butene and (Z)-2-chloro-1,1,1,4,4,4-hexafluoro-2-butene);
(E)-2-chloro-1,1,1,4,4,4-hexafluoro-2-butene;
(Z)-2-chloro-1,1,1,4,4,4-hexafluoro-2-butene;
2,3-dichloro-1,1,1,4,4,4-hexafluorobutane (i.e., a mixture of 2,3-dichloro-1,1,1,4,4,4-hexafluorobutane stereoisomers);
dl-2,3-dichloro-1,1,1,4,4,4-hexafluorobutane;
meso-2,3-dichloro-1,1,1,4,4,4-hexafluorobutane;
2-chloro-1,1,1,3,4,4,4-heptafluorobut-2-ene (i.e., a mixture of (E)-2-chloro-1,1,1,3,4,4,4-heptafluorobut-2-ene and (Z)-2-chloro-1,1,1,3,4,4,4-heptafluorobut-2-ene);
(E)-2-chloro-1,1,1,3,4,4,4-heptafluorobut-2-ene;
(Z)-2-chloro-1,1,1,3,4,4,4-heptafluorobut-2-ene;
1,1,1,2,4,4,4-heptafluorobut-2-ene (i.e., a mixture of (E)-1,1,1,2,4,4,4-heptafluorobut-2-ene and (Z)-1,1,1,2,4,4,4-heptafluorobut-2-ene);
(E)-1,1,1,2,4,4,4-heptafluorobut-2-ene;
(Z)-1,1,1,2,4,4,4-heptafluorobut-2-ene; and
2-chloro-1,1,1,2,4,4,4-heptafluorobutane (i.e., a mixture of 2-chloro-1,1,1,2,4,4,4-heptafluorobutane stereoisomers); and
1,2-dichloro-1,1,4,4,4-pentafluorobut-2-ene (i.e., a mixture of (E)-1,2-dichloro-1,1,4,4,4-pentafluorobut-2-ene and (Z)-1,2-dichloro-1,1,4,4,4-pentafluorobut-2-ene);
(E)-1,2-dichloro-1,1,4,4,4-pentafluorobut-2-ene; and
(Z)-1,2-dichloro-1,1,4,4,4-pentafluorobut-2-ene;
wherein the compound of Formula I is present in an amount effective to form an azeotrope or an azeotrope-like composition with the hydrogen fluoride.

In some embodiments, the compound of Formula I is selected from the group consisting of:
2,3-dichlorohexafluoro-2-butene;
(E)-2,3-dichlorohexafluoro-2-butene;
(Z)-2,3-dichlorohexafluoro-2-butene;
(E)-2-chloro-1,1,1,4,4,4-hexafluoro-2-butene;
(Z)-2-chloro-1,1,1,4,4,4-hexafluoro-2-butene;
dl-2,3-dichloro-1,1,1,4,4,4-hexafluorobutane;
meso-2,3-dichloro-1,1,1,4,4,4-hexafluorobutane;
2-chloro-1,1,1,3,4,4,4-heptafluorobut-2-ene;
2-chloro-1,1,1,2,4,4,4-heptafluorobutane;
(Z)-1,2-dichloro-1,1,4,4,4-pentafluorobut-2-ene;
1,1,1,2,4,4,4-heptafluorobut-2-ene;
wherein the compound of Formula I is present in an amount effective to form an azeotrope or an azeotrope-like composition with the hydrogen fluoride.

In some embodiments, the compound of Formula I is (E)-2,3-dichlorohexafluoro-2-butene, wherein the (E)-2,3-dichlorohexafluoro-2-butene is present in an amount effective to form an azeotrope or an azeotrope-like composition with the hydrogen fluoride.

In some embodiments, the compositions comprise from about 75 to about 99 mole percent hydrogen fluoride, for example, about 75 to about 97, about 75 to about 95, about 75 to about 90, about 75 to about 85, about 75 to about 80, about 80 to about 99, about 80 to about 97, about 80 to about 95, about 80 to about 90, about 80 to about 85, about 85 to about 99, about 85 to about 97, about 85 to about 95, about 85 to about 90, about 90 to about 99, about 90 to about 97, about 90 to about 95, about 95 to about 99, about 95 to about 97, or about 97 to about 99 mole percent hydrogen fluoride and from about 25 to about 1 mole percent (E)-2,3-dichlorohexafluoro-2-butene, for example, about 25 to about 3, about 25 to about 5, about 25 to about 10, about 25 to about 15, about 25 to about 20, about 20 to about 1, about 20 to about 3, about 20 to about 5, about 20 to about 10, about 20 to about 15, about 15 to about 1, about 15 to about 3, about 15 to about 5, about 15 to about 10, about 10 to about 1, about 10 to about 3, about 10 to about 5, about 5 to about 1, about 5 to about 3, or about 3 to about 1 mole percent (E)-2,3-dichlorohexafluoro-2-butene.

In some embodiments, the compositions comprise from about 20 to about 75 weight percent hydrogen fluoride, for example, about 20 to about 70, about 20 to about 60, about 20 to about 50, about 20 to about 40, about 20 to about 30, about 30 to about 75, about 30 to about 70, about 30 to about 60, about 30 to about 50, about 30 to about 40, about 40 to about 75, about 40 to about 70, about 40 to about 60, about 40 to about 50, about 50 to about 75, about 50 to about 70, about 50 to about 60, about 60 to about 75, about 60 to about 70, or about 70 to about 75 weight percent hydrogen fluoride, and from about 80 to about 25 weight percent (E)-2,3-dichlorohexafluoro-2-butene, for example, about 80 to about 30, about 80 to about 40, about 80 to about 50, about 80 to about 60, about 80 to about 70, about 70 to about 25, about 70 to about 30, about 70 to about 40, about 70 to about 50, about 70 to about 60, about 60 to about 25, about 60 to about 30, about 60 to about 40, about 60 to about 50, about 50 to about 25, about 50 to about 30, about 50 to about 40, about 40 to about 25, about 40 to about 30, or about 30 to about 25 weight percent (E)-2,3-dichlorohexafluoro-2-butene.

In some embodiments, the compositions comprising hydrogen fluoride and (E)-2,3-dichlorohexafluoro-2-butene have a boiling point of from about 0° C. to about 130° C., for example, about 0° C. to about 115° C., about 0° C. to about 100° C., about 0° C. to about 75° C., about 0° C. to about 50° C., about 0° C. to about 25° C., about 25° C. to about 130° C., about 25° C. to about 115° C., about 25° C. to about 100° C., about 25° C. to about 75° C., about 25° C. to about 50° C., about 50° C. to about 130° C., about 50° C. to about 115° C., about 50° C. to about 100° C., about 50° C. to about 75° C., about 75° C. to about 130° C., about 75° C. to about 115° C., about 75° C. to about 100° C., about 100° C. to about 130° C., about 100° C. to about 115° C., or about 115° C. to about 130° C., at a pressure of from about 5 psia to about 1000 psia, for example, about 5 psia to about 800 psia, about 5 psia to about 600 psia, about 5 psia to about 400 psia, about 5 psia to about 200 psia, about 5 psia to about 100 psia, about 5 psia to about 50 psia, about 5 psia to about 10 psia, about 10 psia to about 800 psia, about 10 psia to about 600 psia, about 10 psia to about 400 psia, about 10 psia to about 200 psia, about 10 psia to about 100 psia, about 10 psia to about 50 psia, about 50 psia to about 800 psia, about 50 psia to about 600 psia, about 50 psia to about 400 psia, about 50 psia to about 200 psia, about 50 psia to about 100 psia, about 100 psia to about 800 psia, about 100 psia to about 600 psia, about 100 psia to about 400 psia, about 100 psia to about 200 psia, about 200 psia to about 800 psia, about 200 psia to about 600 psia, about 200 psia to about 400 psia, about 400 psia to about 800 psia, about 400 psia to about 600 psia, or about 600 psia to about 800 psia.

In some embodiments, the compound of Formula I is (Z)-2,3-dichlorohexafluoro-2-butene, wherein the (Z)-2,3-dichlorohexafluoro-2-butene is present in an amount effective to form an azeotrope or an azeotrope-like composition with the hydrogen fluoride.

In some embodiments, the compositions comprise from about 75 to about 99 mole percent hydrogen fluoride, for example, about 75 to about 97, about 75 to about 95, about 75 to about 90, about 75 to about 85, about 75 to about 80, about 80 to about 99, about 80 to about 97, about 80 to about 95, about 80 to about 90, about 80 to about 85, about 85 to about 99, about 85 to about 97, about 85 to about 95, about 85 to about 90, about 90 to about 99, about 90 to about 97, about 90 to about 95, about 95 to about 99, about 95 to about 97, or about 97 to about 99 mole percent hydrogen fluoride and from about 25 to about 1 mole percent (Z)-2,3-dichlorohexafluoro-2-butene, for example, about 25 to about 3, about 25 to about 5, about 25 to about 10, about 25 to about 15, about 25 to about 20, about 20 to about 1, about 20 to about 3, about 20 to about 5, about 20 to about 10, about 20 to about 15, about 15 to about 1, about 15 to about 3, about 15 to about 5, about 15 to about 10, about 10 to about 1, about 10 to about 3, about 10 to about 5, about 5 to about 1, about 5 to about 3, or about 3 to about 1 mole percent (Z)-2,3-dichlorohexafluoro-2-butene.

In some embodiments, the compositions comprise from about 20 to about 75 weight percent hydrogen fluoride, for example, about 20 to about 60, about 20 to about 50, about 20 to about 40, about 20 to about 30, about 30 to about 75, about 30 to about 60, about 30 to about 50, about 30 to about 40, about 40 to about 75, about 40 to about 60, about 40 to about 50, about 50 to about 75, about 50 to about 60, about 60 to about 75 weight percent hydrogen fluoride, and from about 80 to about 25 weight percent (Z)-2,3-dichlorohexafluoro-2-butene, for example, about 80 to about 30, about 80 to about 40, about 80 to about 50, about 80 to about 60, about 80 to about 70, about 70 to about 25, about 70 to about 30, about 70 to about 40, about 70 to about 50, about 70 to about 60, about 60 to about 25, about 60 to about 30, about 60 to about 40, about 60 to about 50, about 50 to about 25, about 50 to about 30, about 50 to about 40, about 40 to about 25, about 40 to about 30, or about 30 to about 25 weight percent (Z)-2,3-dichlorohexafluoro-2-butene.

In some embodiments, the compositions comprising hydrogen fluoride and (Z)-2,3-dichlorohexafluoro-2-butene have a boiling point of from about 0° C. to about 130° C., for example, about 0° C. to about 115° C., about 0° C. to about 100° C., about 0° C. to about 75° C., about 0° C. to about 50° C., about 0° C. to about 25° C., about 25° C. to about 130° C., about 25° C. to about 115° C., about 25° C. to about 100° C., about 25° C. to about 75° C., about 25° C. to about 50° C., about 50° C. to about 130° C., about 50° C. to about 115° C., about 50° C. to about 100° C., about 50° C. to about 75° C., about 75° C. to about 130° C., about 75° C. to about 115° C., about 75° C. to about 100° C., about 100° C. to about 130° C., about 100° C. to about 115° C., or about 115° C. to about 130° C., at a pressure of from about 5 psia to about 1000 psia, for example, about 5 psia to about 800 psia, about 5 psia to about 600 psia, about 5 psia to about 400 psia, about 5 psia to about 200 psia, about 5 psia to about 100 psia, about 5 psia to about 50 psia, about 5 psia to about 10 psia, about 10 psia to about 800 psia, about 10 psia to about 600 psia, about 10 psia to about 400 psia, about 10 psia to about 200 psia, about 10 psia to about 100 psia, about 10 psia to about 50 psia, about 50 psia to about 800 psia, about 50 psia to about 600 psia, about 50 psia to about 400 psia, about 50 psia to about 200 psia, about 50 psia to about 100 psia, about 100 psia to about 800 psia, about 100 psia to about 600 psia, about 100 psia to about 400 psia, about 100 psia to about 200 psia, about 200 psia to about 800 psia, about 200 psia to about 600 psia, about 200 psia to about 400 psia, about 400 psia to about 800 psia, about 400 psia to about 600 psia, or about 600 psia to about 800 psia.

In some embodiments, the compound of Formula I is a mixture of (E)-2,3-dichlorohexafluoro-2-butene and (Z)-2,3-dichlorohexafluoro-2-butene isomers, wherein the mixture of 2,3-dichlorohexafluoro-2-butene are present in an amount effective to form an azeotrope or an azeotrope-like composition with the hydrogen fluoride.

In some embodiments, the ratio of (Z)-2,3-dichlorohexafluoro-2-butene to (E)-2,3-dichlorohexafluoro-2-butene is from about 0.1:99.9 to about 99.9:0.1. In some embodiments, the ratio of (Z)-2,3-dichlorohexafluoro-2-butene to (E)-2,3-dichlorohexafluoro-2-butene is from about 40:60 to about 60:40. In some embodiments, the ratio of (Z)-2,3-dichlorohexafluoro-2-butene to (E)-2,3-dichlorohexafluoro-2-butene is about 45:55.

In some embodiments, the compositions comprise from about 75 to about 99 mole percent hydrogen fluoride, for example, about 75 to about 97, about 75 to about 95, about 75 to about 90, about 75 to about 87, about 87 to about 99, about 87 to about 97, about 87 to about 95, about 87 to about 90, about 90 to about 99, about 90 to about 97, about 90 to about 95, about 95 to about 99, about 95 to about 97, or about 97 to about 99 mole percent hydrogen fluoride, and from about 25 to about 1 mole percent 2,3-dichlorohexafluoro-2-butene (i.e., a mixture of (E) and (Z) isomers), for example, about 25 to about 3, about 25 to about 5, about 25 to about 10, about 25 to about 13, about 13 to about 1, about 13 to about 3, about 13 to about 5, about 13 to about 10, about 10 to about 1, about 10 to about 3, about 10 to about 5, about 5 to about 1, about 5 to about 3, or about 3 to about 1 mole percent 2,3-dichlorohexafluoro-2-butene.

In some embodiments, the compositions comprise from about 20 to about 75 weight percent hydrogen fluoride, for example, about 20 to about 70, about 20 to about 60, about 20 to about 50, about 20 to about 40, about 20 to about 30, about 30 to about 75, about 30 to about 70, about 30 to about 60, about 30 to about 50, about 30 to about 40, about 40 to about 75, about 40 to about 70, about 40 to about 60, about 40 to about 50, about 50 to about 75, about 50 to about 70, about 50 to about 60, about 60 to about 75, about 60 to about 70, or about 70 to about 75 weight percent hydrogen fluoride, and from about 80 to about 25 weight percent 2,3-dichlorohexafluoro-2-butene (i.e., a mixture of (E) and (Z) isomers), for example, about 80 to about 30, about 80 to about 40, about 80 to about 50, about 80 to about 60, about 80 to about 70, about 70 to about 25, about 70 to about 30, about 70 to about 40, about 70 to about 50, about 70 to about 60, about 60 to about 25, about 60 to about 30, about 60 to about 40, about 60 to about 50, about 50 to about 25, about 50 to about 30, about 50 to about 40, about 40 to about 25, about 40 to about 30, or about 30 to about 25 weight percent 2,3-dichlorohexafluoro-2-butene.

In some embodiments, the compositions comprising hydrogen fluoride and 2,3-dichlorohexafluoro-2-butene (i.e., a mixture of (E)- and (Z)-isomers) have a boiling point of from about 0° C. to about 130° C., for example, about 0° C. to about 115° C., about 0° C. to about 100° C., about 0° C. to about 75° C., about 0° C. to about 50° C., about 0° C. to about 25° C., about 25° C. to about 130° C., about 25° C. to about 115° C., about 25° C. to about 100° C., about 25° C. to about 75° C., about 25° C. to about 50° C., about 50° C. to about 130° C., about 50° C. to about 115° C., about 50° C. to about 100° C., about 50° C. to about 75° C., about 75° C. to about 130° C., about 75° C. to about 115° C., about 75° C. to about 100° C., about 100° C. to about 130° C., about 100° C. to about 115° C., or about 115° C. to about 130° C., at a pressure of from about 5 psia to about 1100 psia, for example, about 5 psia to about 1000 psia, for example, about 5 psia to about 800 psia, about 5 psia to about 600 psia, about 5 psia to about 400 psia, about 5 psia to about 200 psia, about 5 psia to about 100 psia, about 5 psia to about 50 psia, about 5 psia to about 10 psia, about 10 psia to about 1100 psia, about 10 psia to about 1000 psia, about 10 psia to about 800 psia, about 10 psia to about 600 psia, about 10 psia to about 400 psia, about 10 psia to about 200 psia, about 10 psia to about 100 psia, about 10 psia to about 50 psia, about 50 psia to about 800 psia, about 50 psia to about 600 psia, about 50 psia to about 400 psia, about 50 psia to about 200 psia, about 50 psia to about 100 psia, about 100 psia to about 1100 psia, about 100 psia to about 1000 psia, about 100 psia to about 800 psia, about 100 psia to about 600 psia, about 100 psia to about 400 psia, about 100 psia to about 200 psia, about 200 psia to about 1100 psia, about 200 psia to about 1000 psia, about 200 psia to about 800 psia, about 200 psia to about 600 psia, about 200 psia to about 400 psia, about 400 psia to about 1100 psia, about 400 psia to about 1000 psia, about 400 psia to about 800 psia, about 400 psia to about 600 psia, about 600 psia to about 1100 psia, about 600 psia to about 1000 psia, about 600 psia to about 800 psia, about 800 psia to about 1100 psia, about 800 psia to about 1000 psia, or about 1000 psia to about 1100 psia.

In some embodiments, the compound of Formula I is (E)-2-chloro-1,1,1,4,4,4-hexafluoro-2-butene, wherein the (E)-2-chloro-1,1,1,4,4,4-hexafluoro-2-butene is present in an amount effective to form an azeotrope or an azeotrope-like composition with the hydrogen fluoride.

In some embodiments, the compositions comprise from about 60 to about 99 mole percent hydrogen fluoride, for example, about 60 to about 95, about 60 to about 90, about 60 to about 80, about 60 to about 70, about 60 to about 65, about 65 to about 99, about 65 to about 95, about 65 to about 90, about 65 to about 80, about 65 to about 70, about 70 to about 99, about 70 to about 95, about 70 to about 90, about 70 to about 80, about 80 to about 99, about 80 to about 95, about 80 to about 90, about 90 to about 99, about 90 to about 95, or about 95 to about 99 mole percent hydrogen fluoride and from about 40 to about 1 mole percent (E)-2-chloro-1,1,1,4,4,4-hexafluoro-2-butene, for example, about 40 to about 5, about 40 to about 10, about 40 to about 20, about 40 to about 30, about 40 to about 35, about 35 to about 1, about 35 to about 5, about 35 to about 10, about 35 to about 20, about 35 to about 30, about 30 to about 1, about 30 to about 5, about 30 to about 10, about 30 to about 20, about 20 to about 1, about 20 to about 5, about 20 to about 10, about 10 to about 1, about 10 to about 5, or about 5 to about 1 mole percent (E)-2-chloro-1,1,1,4,4,4-hexafluoro-2-butene.

In some embodiments, the compositions comprise from about 15 to about 60 weight percent hydrogen fluoride, for example, about 15 to about 50, about 15 to about 40, about 15 to about 30, about 15 to about 20, about 20 to about 60, about 20 to about 50, about 20 to about 40, about 20 to about 30, about 30 to about 60, about 30 to about 50, about 30 to about 40, about 40 to about 60, about 40 to about 50, or about 50 to about 60 weight percent hydrogen fluoride, and from about 85 to about 40 weight percent (E)-2-chloro-1,1, 1,4,4,4-hexafluoro-2-butene, for example, about 85 to about 50, about 85 to about 60, about 85 to about 70, about 85 to about 80, about 80 to about 40, about 80 to about 50, about 80 to about 60, about 80 to about 70, about 70 to about 40, about 70 to about 50, about 70 to about 60, about 60 to about 40, about 60 to about 50, or about 60 to about 40 weight percent (E)-2-chloro-1,1,1,4,4,4-hexafluoro-2-butene.

In some embodiments, the compositions comprising hydrogen fluoride and (E)-2-chloro-1,1,1,4,4,4-hexafluoro-2-butene have a boiling point of from about −25° C. to about 145° C., for example, about −25° C. to about 140° C., about −25° C. to about 125° C., about −25° C. to about 100° C., about −25° C. to about 50° C., about −25° C. to about 25° C., about −25° C. to about 0° C., about −25° C. to about −20° C., about −20° C. to about 145° C., about −20° C. to about 140° C., about −20° C. to about 125° C., about −20° C. to about 100° C., about −20° C. to about 50° C., about −20° C. to about 25° C., about −20° C. to about 0° C., about 0° C. to about 145° C., about 0° C. to about 140° C., about 0° C. to about 125° C., about 0° C. to about 100° C., about 0° C. to about 50° C., about 0° C. to about 25° C., about 20° C. to about 145° C., about 20° C. to about 140° C., about 20° C. to about 125° C., about 20° C. to about 100° C., about 20° C. to about 50° C., about 50° C. to about 145° C., about 50° C. to about 140° C., about 50° C. to about 125° C., about 50° C. to about 100° C., about 100° C. to about 145° C., about 100° C. to about 140° C., about 100° C. to about 125° C., about 125° C. to about 145° C., about 125° C. to about 140° C., or about 125° C. to about 145° C. at a pressure of from about 1 psia to about 800 psia, for example, about 1 psia to about 600 psia, about 1 psia to about 400 psia, about 1 psia to about 200 psia, about 1 psia to about 100 psia, about 1 psia to about 50 psia, about 50 psia to about 800 psia, about 50 psia to about 600 psia, about 50 psia to about 400 psia, about 50 psia to about 200 psia, about 50 psia to about 100 psia, about 100 psia to about 800 psia, about 100 psia to about 600 psia, about 100 psia to about 400 psia, about 100 psia to about 200 psia, about 200 psia to about 800 psia, about 200 psia to about 600 psia, about 200 psia to about 400 psia, about 400 psia to about 800 psia, about 400 psia to about 600 psia, or about 600 psia to about 800 psia.

In some embodiments, the compound of Formula I is (Z)-2-chloro-1,1,1,4,4,4-hexafluoro-2-butene, wherein the (Z)-2-chloro-1,1,1,4,4,4-hexafluoro-2-butene is present in an amount effective to form an azeotrope or an azeotrope-like composition with the hydrogen fluoride.

In some embodiments, the compositions comprise from about 65 to about 95 mole percent hydrogen fluoride, for example, about 65 to about 90, about 65 to about 80, about 65 to about 70, about 70 to about 95, about 70 to about 90, about 70 to about 80, about 80 to about 95, about 80 to about 90, or about 80 to about 95 mole percent hydrogen fluoride and from about 35 to about 5 mole percent (Z)-2-chloro-1,1,1,4,4,4-hexafluoro-2-butene, for example, about 35 to about 10, about 35 to about 20, about 35 to about 30, about 30 to about 5, about 30 to about 10, about 30 to about 20, about 20 to about 5, about 20 to about 10, or about 10 to about 5 mole percent (Z)-2-chloro-1,1,1,4,4,4-hexafluoro-2-butene.

In some embodiments, the compositions comprise from about 15 to about 50 weight percent hydrogen fluoride, for example, about 15 to about 40, about 15 to about 30, about 15 to about 20, about 20 to about 50, about 20 to about 40, about 20 to about 30, about 30 to about 50, about 30 to about 40, or about 40 to about 50 weight percent hydrogen fluoride, and from about 85 to about 50 weight percent (Z)-2-chloro-1,1,1,4,4,4-hexafluoro-2-butene, for example, about 85 to about 60, about 85 to about 70, about 85 to about 80, about 80 to about 50, about 80 to about 60, about 80 to about 70, about 70 to about 50, about 70 to about 60, or about 60 to about 50 weight percent (Z)-2-chloro-1,1,1,4,4,4-hexafluoro-2-butene.

In some embodiments, the compositions comprising hydrogen fluoride and (Z)-2-chloro-1,1,1,4,4,4-hexafluoro-2-butene have a boiling point of from about −25° C. to about 145° C., for example, about −25° C. to about 140° C., about −25° C. to about 125° C., about −25° C. to about 100° C., about −25° C. to about 50° C., about −25° C. to about 25° C., about −25° C. to about 0° C., about −25° C. to about −20° C., about −20° C. to about 145° C., about −20° C. to about 140° C., about −20° C. to about 125° C., about −20° C. to about 100° C., about −20° C. to about 50° C., about −20° C. to about 25° C., about −20° C. to about 0° C., about 0° C. to about 145° C., about 0° C. to about 140° C., about 0° C. to about 125° C., about 0° C. to about 100° C., about 0° C. to about 50° C., about 0° C. to about 25° C., about 20° C. to about 145° C., about 20° C. to about 140° C., about 20° C. to about 125° C., about 20° C. to about 100° C., about 20° C. to about 50° C., about 50° C. to about 145° C., about 50° C. to about 140° C., about 50° C. to about 125° C., about 50° C. to about 100° C., about 100° C. to about 145° C., about 100° C. to about 140° C., about 100° C. to about 125° C., about 125° C. to about 145° C., about 125° C. to about 140° C., or about 125° C. to about 145° C. at a pressure of from about 1 psia to about 850 psia, for example, about 1 psia to about 800 psia, about 1 psia to about 600 psia, about 1 psia to about 400 psia, about 1 psia to about 200 psia, about 1 psia to about 100 psia, about 1 psia to about 50 psia, about 50 psia to about 850 psia, about 50 psia to about 800 psia, about 50 psia to about 600 psia, about 50 psia to about 400 psia, about 50 psia to about 200 psia, about 50 psia to about 100 psia, about 100 psia to about 850 psia, about 100 psia to about 800 psia, about 100 psia to about 600 psia, about 100 psia to about 400 psia, about 100 psia to about 200 psia, about 200 psia to about 850 psia, about 200 psia to about 800 psia, about 200 psia to about 600 psia, about 200 psia to about 400 psia, about 400 psia to about 850 psia, about 400 psia to about 800 psia, about 400 psia to about 600 psia, about 600 psia to about 850 psia, about 600 psia to about 800 psia, or about 800 psia to about 850 psia.

In some embodiments, the compound of Formula I is 2,3-dichloro-1,1,1,4,4,4-hexafluorobutane, wherein the 2,3-dichloro-1,1,1,4,4,4-hexafluorobutane is present in an amount effective to form an azeotrope or an azeotrope-like composition with the hydrogen fluoride.

In some embodiments, the 2,3-dichloro-1,1,1,4,4,4-hexafluorobutane is dl-2,3-dichloro-1,1,1,4,4,4-hexafluorobutane.

In some embodiments, the compositions comprise from about 75 to about 99 mole percent hydrogen fluoride, for example, about 75 to about 97, about 75 to about 95, about 75 to about 90, about 75 to about 85, about 75 to about 80, about 80 to about 99, about 80 to about 97, about 80 to about 95, about 80 to about 90, about 80 to about 85, about 85 to about 99, about 85 to about 97, about 85 to about 95, about 85 to about 90, about 90 to about 99, about 90 to about 97, about 90 to about 95, about 95 to about 99, about 95 to about 97, or about 97 to about 99 mole percent hydrogen fluoride and from about 25 to about 1 mole percent dl-2,3-dichloro-1,1,1,4,4,4-hexafluorobutane, for example, about 25 to about 3, about 25 to about 5, about 25 to about 10, about 25 to about 15, about 25 to about 20, about 20 to about 1, about 20 to about 3, about 20 to about 5, about 20 to about 10, about 20 to about 15, about 15 to about 1, about 15 to about 3, about 15 to about 5, about 15 to about 10, about 10 to about 1, about 10 to about 3, about 10 to about 5, about 5 to about 1, about 5 to about 3, or about 3 to about 1 mole percent dl-2,3-dichloro-1,1,1,4,4,4-hexafluorobutane.

In some embodiments, the compositions comprise from about 20 to about 75 weight percent hydrogen fluoride, for example, about 20 to about 65, about 20 to about 55, about 20 to about 45, about 20 to about 35, about 20 to about 25, about 25 to about 75, about 25 to about 65, about 25 to about 55, about 25 to about 45, about 25 to about 35, about 35 to about 75, about 35 to about 65, about 35 to about 55, about 35 to about 45, about 45 to about 75, about 45 to about 65, about 45 to about 55, about 55 to about 75, about 55 to about 65, or about 65 to about 75 weight percent hydrogen fluoride and from about 80 to about 25 weight percent dl-2,3-dichloro-1,1,1,4,4,4-hexafluorobutane, for example, about 80 to about 35, about 80 to about 45, about 80 to about 55, about 80 to about 65, about 80 to about 75, about 75 to about 25, about 75 to about 35, about 75 to about 45, about 75 to about 55, about 75 to about 65, about 65 to about 25, about 65 to about 35, about 65 to about 45, about 65 to about 55, about 55 to about 25, about 55 to about 35, about 55 to about 45, about 45 to about 25, about 45 to about 35, or about 35 to about 25 weight percent dl-2,3-dichloro-1,1,1,4,4,4-hexafluorobutane.

In some embodiments, the compositions comprising hydrogen fluoride and dl-2,3-dichloro-1,1,1,4,4,4-hexafluorobutane have a boiling point of from about 0° C. to about 140° C., for example, about 0° C. to about 120° C., about 0° C. to about 100° C., about 0° C. to about 80° C., about 0° C. to about 60° C., about 0° C. to about 40° C., about 0° C. to about 20° C., about 20° C. to about 140° C., about 20° C. to about 120° C., about 20° C. to about 100° C., about 20° C. to about 80° C., about 20° C. to about 60° C., about 20° C. to about 40° C., about 40° C. to about 140° C., about 40° C. to about 120° C., about 40° C. to about 100° C., about 40° C. to about 80° C., about 40° C. to about 60° C., about 60° C. to about 140° C., about 60° C. to about 120° C., about 60° C. to about 100° C., about 60° C. to about 80° C., about 80° C. to about 140° C., about 80° C. to about 120° C., about 80° C. to about 100° C., about 100° C. to about 140° C., about 100° C. to about 120° C., or about 120° C. to about 140° C., at a pressure of from about 5 psia to about 1000 psia, for example, about 5 psia to about 900 psia, about 5 psia to about 700 psia, about 5 psia to about 500 psia, about 5 psia to about 200 psia, about 5 psia to about 100 psia, about 5 psia to about 50 psia, about 50 psia to about 1000 psia, about 50 psia to about 900 psia, about 50 psia to about 700 psia, about 50 psia to about 500 psia, about 50 psia to about 200 psia, about 50 psia to about 100 psia, about 100 psia to about 1000 psia, about 100 psia to about 900 psia, about 100 psia to about 700 psia, about 100 psia to about 500 psia, about 100 psia to about 200 psia, about 200 psia to about 1000 psia, about 200 psia to about 900 psia, about 200 psia to about 700 psia, about 200 psia to about 500 psia, about 500 psia to about 1000 psia, about 500 psia to about 900 psia, about 500 psia to about 700 psia, about 700 psia to about 1000 psia, about 700 psia to about 900 psia, or about 900 psia to about 1000 psia.

In some embodiments, the 2,3-dichloro-1,1,1,4,4,4-hexafluorobutane is meso-2,3-dichloro-1,1,1,4,4,4-hexafluorobutane.

In some embodiments, the compositions comprise from about 75 to about 99 mole percent hydrogen fluoride, for example, about 75 to about 97, about 75 to about 95, about 75 to about 90, about 75 to about 85, about 75 to about 80, about 80 to about 99, about 80 to about 97, about 80 to about 95, about 80 to about 90, about 80 to about 85, about 85 to about 99, about 85 to about 97, about 85 to about 95, about 85 to about 90, about 90 to about 99, about 90 to about 97, about 90 to about 95, about 95 to about 99, about 95 to about 97, or about 97 to about 99 mole percent hydrogen fluoride and from about 25 to about 1 mole percent meso-2,3-dichloro-1,1,1,4,4,4-hexafluorobutane, for example, about 25 to about 3, about 25 to about 5, about 25 to about 10, about 25 to about 15, about 25 to about 20, about 20 to about 1, about 20 to about 3, about 20 to about 5, about 20 to about 10, about 20 to about 15, about 15 to about 1, about 15 to about 3, about 15 to about 5, about 15 to about 10, about 10 to about 1, about 10 to about 3, about 10 to about 5, about 5 to about 1, about 5 to about 3, or about 3 to about 1 mole percent meso-2,3-dichloro-1,1,1,4,4,4-hexafluorobutane.

In some embodiments, the compositions comprise from about 20 to about 85 weight percent hydrogen fluoride, for example, about 20 to about 80, about 20 to about 60, about 20 to about 40, about 40 to about 85, about 40 to about 80, about 40 to about 60, about 60 to about 85, about 60 to about 80, or about 80 to about 85 weight percent hydrogen fluoride and from about 80 to about 15 weight percent meso-2,3-dichloro-1,1,1,4,4,4-hexafluorobutane, for example about 80 to about 20, about 80 to about 40, about 80 to about 60, about 60 to about 15, about 60 to about 20, about 60 to about 40, about 40 to about 15, about 40 to about 20, or about 20 to about 15 weight percent meso-2,3-dichloro-1,1,1,4,4,4-hexafluorobutane.

In some embodiments, the compositions comprising hydrogen fluoride and meso-2,3-dichloro-1,1,1,4,4,4-hexafluorobutane have a boiling point of from about 0° C. to about 140° C., for example, about 0° C. to about 120° C., about 0° C. to about 100° C., about 0° C. to about 80° C., about 0° C. to about 60° C., about 0° C. to about 40° C., about 0° C. to about 20° C., about 20° C. to about 140° C., about 20° C. to about 120° C., about 20° C. to about 100° C., about 20° C. to about 80° C., about 20° C. to about 60° C., about 20° C. to about 40° C., about 40° C. to about 140° C., about 40° C. to about 120° C., about 40° C. to about 100° C., about 40° C. to about 80° C., about 40° C. to about 60° C., about 60° C. to about 140° C., about 60° C. to about 120° C., about 60° C. to about 100° C., about 60° C. to about 80° C., about 80° C. to about 140° C., about 80° C. to about 120° C., about 80° C. to about 100° C., about 100° C. to about 140° C., about 100° C. to about 120° C., or about 120° C. to about 140° C., at a pressure of from about 5 psia to about 1000 psia, for example, about 5 psia to about 800 psia, about 5 psia to about 600 psia, about 5 psia to about 400 psia, about 5 psia to about 200 psia, about 5 psia to about 100 psia, about 5 psia to about 50 psia, about 5 psia to about 10 psia, about 10 psia to about 800 psia, about 10 psia to about 600 psia, about 10 psia to about 400 psia, about 10 psia to about 200 psia, about 10 psia to about 100 psia, about 10 psia to about 50 psia, about 50 psia to about 800 psia, about 50 psia to about 600 psia, about 50 psia to about 400 psia, about 50 psia to about 200 psia, about 50 psia to about 100 psia, about 100 psia to about 800 psia, about 100 psia to about 600 psia, about 100 psia to about 400 psia, about 100 psia to about 200 psia, about 200 psia to about 800 psia, about 200 psia to about 600 psia, about 200 psia to about 400 psia, about 400 psia to about 800 psia, about 400 psia to about 600 psia, or about 600 psia to about 800 psia.

In some embodiments, the compound of Formula I is 2-chloro-1,1,1,3,4,4,4-heptafluorobut-2-ene, wherein the 2-chloro-1,1,1,3,4,4,4-heptafluorobut-2-ene is present in an amount effective to form an azeotrope or an azeotrope-like composition with the hydrogen fluoride.

In some embodiments, the compositions comprise from about 90 to about 60 mole percent hydrogen fluoride, for example, about 90 to about 65, about 90 to about 70, about 90 to about 75, about 90 to about 80, about 90 to about 85, about 85 to about 60, about 85 to about 65, about 85 to about 70, about 85 to about 75, about 85 to about 80, about 80 to about 60, about 80 to about 65, about 80 to about 70, about 80 to about 75, about 75 to about 60, about 75 to about 65, about 75 to about 70, about 70 to about 60, about 70 to about 65, or about 65 to about 60 mole percent hydrogen fluoride and from about 10 to about 40 mole percent 2-chloro-1,1,1,3,4,4,4-heptafluorobut-2-ene, for example, about 10 to about 35, about 10 to about 30, about 10 to about 25, about 10 to about 20, about 10 to about 15, about 15 to about 40, about 15 to about 35, about 15 to about 30, about 15 to about 25, about 15 to about 20, about 20 to about 40, about 20 to about 35, about 20 to about 30, about 20 to about 25, about 25 to about 40, about 25 to about 35, about 25 to about 30, about 30 to about 40, about 30 to about 35, or about 35 to about 40 mole percent 2-chloro-1,1,1,3,4,4,4-heptafluorobut-2-ene.

In some embodiments, the compositions comprise from about 10 to about 45 weight percent hydrogen fluoride, for example, about 10 to about 40, about 10 to about 30, about 10 to about 20, about 10 to about 15, about 15 to about 45, about 15 to about 40, about 15 to about 30, about 15 to about 20, about 20 to about 45, about 20 to about 40, about 20 to about 30, about 30 to about 45, about 30 to about 40, or about 40 to about 45 weight percent hydrogen fluoride and from about 90 to about 55 weight percent 2-chloro-1,1,1,3,4,4,4-heptafluorobut-2-ene, for example, about 90 to about 60, about 90 to about 70, about 90 to about 80, about 90 to about 85, about 85 to about 55, about 85 to about 60, about 85 to about 70, about 85 to about 80, about 80 to about 55, about 80 to about 60, about 80 to about 70, about 70 to about 55, about 70 to about 60, or about 60 to about 55 weight percent 2-chloro-1,1,1,3,4,4,4-heptafluorobut-2-ene.

In some embodiments, the compositions comprising hydrogen fluoride and 2-chloro-1,1,1,3,4,4,4-heptafluorobut-2-ene have a boiling point of from about −25° C. to about 145° C., for example, about −25° C. to about 140° C., about −25° C. to about 125° C., about −25° C. to about 100° C., about −25° C. to about 50° C., about −25° C. to about 25°

C., about −25° C. to about 0° C., about −25° C. to about −20° C., about −20° C. to about 145° C., about −20° C. to about 140° C., about −20° C. to about 125° C., about −20° C. to about 100° C., about −20° C. to about 50° C., about −20° C. to about 25° C., about −20° C. to about 0° C., about 0° C. to about 145° C., about 0° C. to about 140° C., about 0° C. to about 125° C., about 0° C. to about 100° C., about 0° C. to about 50° C., about 0° C. to about 25° C., about 20° C. to about 145° C., about 20° C. to about 140° C., about 20° C. to about 125° C., about 20° C. to about 100° C., about 20° C. to about 50° C., about 50° C. to about 145° C., about 50° C. to about 140° C., about 50° C. to about 125° C., about 50° C. to about 100° C., about 100° C. to about 145° C., about 100° C. to about 140° C., about 100° C. to about 125° C., about 125° C. to about 145° C., about 125° C. to about 140° C., or about 125° C. to about 145° C. at a pressure of from about 1 psia to about 850 psia, for example, about 1 psia to about 800 psia, about 1 psia to about 600 psia, about 1 psia to about 400 psia, about 1 psia to about 200 psia, about 1 psia to about 100 psia, about 1 psia to about 50 psia, about 50 psia to about 850 psia, about 50 psia to about 800 psia, about 50 psia to about 600 psia, about 50 psia to about 400 psia, about 50 psia to about 200 psia, about 50 psia to about 100 psia, about 100 psia to about 850 psia, about 100 psia to about 800 psia, about 100 psia to about 600 psia, about 100 psia to about 400 psia, about 100 psia to about 200 psia, about 200 psia to about 850 psia, about 200 psia to about 800 psia, about 200 psia to about 600 psia, about 200 psia to about 400 psia, about 400 psia to about 850 psia, about 400 psia to about 800 psia, about 400 psia to about 600 psia, about 600 psia to about 850 psia, about 600 psia to about 800 psia, or about 800 psia to about 850 psia.

In some embodiments, the compound of Formula I is 2-chloro-1,1,1,2,4,4,4-heptafluorobutane, wherein the 2-chloro-1,1,1,2,4,4,4-heptafluorobutane is present in an amount effective to form an azeotrope or an azeotrope-like composition with the hydrogen fluoride.

In some embodiments, the compositions comprise from about 60 to about 95 mole percent hydrogen fluoride, for example, about 60 to about 90, about 60 to about 80, about 60 to about 70, about 60 to about 65, about 65 to about 95, about 65 to about 90, about 65 to about 80, about 65 to about 70, about 70 to about 95, about 70 to about 90, about 70 to about 80, about 80 to about 95, about 80 to about 90, or about 80 to about 95 mole percent hydrogen fluoride and from about 40 to about 5 mole percent 2-chloro-1,1,1,2,4,4,4-heptafluorobutane, for example, about 40 to about 10, about 40 to about 20, about 40 to about 30, about 40 to about 35, about 35 to about 5, about 35 to about 10, about 35 to about 20, about 35 to about 30, about 30 to about 5, about 30 to about 10, about 30 to about 20, about 20 to about 5, about 20 to about 10, or about 10 to about 5 mole percent 2-chloro-1,1,1,2,4,4,4-heptafluorobutane.

In some embodiments, the compositions comprise from about 60 to about 10 weight percent hydrogen fluoride, for example, about 60 to about 20, about 60 to about 30, about 60 to about 40, about 60 to about 50, about 50 to about 10, about 50 to about 20, about 50 to about 30, about 50 to about 40, about 40 to about 10, about 40 to about 20, about 40 to about 30, about 30 to about 10, about 30 to about 20, or about 20 to about 10 weight percent hydrogen fluoride and from about 40 to about 90 weight percent 2-chloro-1,1,1,2,4,4,4-heptafluorobutane, for example, about 40 to about 80, about 40 to about 70, about 40 to about 60, about 40 to about 50, about 50 to about 90, about 50 to about 80, about 50 to about 70, about 50 to about 60, about 60 to about 90, about 60 to about 80, about 60 to about 70, about 70 to about 90, about 70 to about 80, or about 80 to about 90 weight percent 2-chloro-1,1,1,2,4,4,4-heptafluorobutane.

In some embodiments, the compositions comprising hydrogen fluoride and 2-chloro-1,1,1,2,4,4,4-heptafluorobutane have a boiling point of from about −25° C. to about 145° C., for example, about −25° C. to about 140° C., about −25° C. to about 125° C., about −25° C. to about 100° C., about −25° C. to about 50° C., about −25° C. to about 25° C., about −25° C. to about 0° C., about −25° C. to about −20° C., about −20° C. to about 145° C., about −20° C. to about 140° C., about −20° C. to about 125° C., about −20° C. to about 100° C., about −20° C. to about 50° C., about −20° C. to about 25° C., about −20° C. to about 0° C., about 0° C. to about 145° C., about 0° C. to about 140° C., about 0° C. to about 125° C., about 0° C. to about 100° C., about 0° C. to about 50° C., about 0° C. to about 25° C., about 20° C. to about 145° C., about 20° C. to about 140° C., about 20° C. to about 125° C., about 20° C. to about 100° C., about 20° C. to about 50° C., about 50° C. to about 145° C., about 50° C. to about 140° C., about 50° C. to about 125° C., about 50° C. to about 100° C., about 100° C. to about 145° C., about 100° C. to about 140° C., about 100° C. to about 125° C., about 125° C. to about 145° C., about 125° C. to about 140° C., or about 125° C. to about 145° C. at a pressure of from about 1 psia to about 800 psia, for example, about 1 psia to about 600 psia, about 1 psia to about 400 psia, about 1 psia to about 200 psia, about 1 psia to about 100 psia, about 1 psia to about 50 psia, about 50 psia to about 800 psia, about 50 psia to about 600 psia, about 50 psia to about 400 psia, about 50 psia to about 200 psia, about 50 psia to about 100 psia, about 100 psia to about 800 psia, about 100 psia to about 600 psia, about 100 psia to about 400 psia, about 100 psia to about 200 psia, about 200 psia to about 800 psia, about 200 psia to about 600 psia, about 200 psia to about 400 psia, about 400 psia to about 800 psia, about 400 psia to about 600 psia, or about 600 psia to about 800 psia.

In some embodiments, the compound of Formula I is (Z)-1,2-dichloro-1,1,4,4,4-pentafluorobut-2-ene, wherein the (Z)-1,2-dichloro-1,1,4,4,4-pentafluorobut-2-ene is present in an amount effective to form an azeotrope or an azeotrope-like composition with the hydrogen fluoride.

In some embodiments, the compositions comprise from about 80 to about 99 mole percent hydrogen fluoride, for example, about 80 to about 97, about 80 to about 95, about 80 to about 90, about 80 to about 85, about 85 to about 99, about 85 to about 97, about 85 to about 95, about 85 to about 90, about 90 to about 99, about 90 to about 97, about 90 to about 95, about 95 to about 99, about 95 to about 97, or about 97 to about 99 mole percent hydrogen fluoride and from about 20 to about 1 mole percent (Z)-1,2-dichloro-1,1,4,4,4-pentafluorobut-2-ene, for example, about 20 to about 3, about 20 to about 5, about 20 to about 10, about 20 to about 15, about 15 to about 1, about 15 to about 3, about 15 to about 5, about 15 to about 10, about 10 to about 1, about 10 to about 3, about 10 to about 5, about 5 to about 1, about 5 to about 3, or about 3 to about 1 mole percent (Z)-1,2-dichloro-1,1,4,4,4-pentafluorobut-2-ene.

In some embodiments, the compositions comprise from about 80 to about 25 weight percent hydrogen fluoride, for example, about 80 to about 35, about 80 to about 45, about 80 to about 55, about 80 to about 65, about 80 to about 75, about 80 to about 25, about 75 to about 25, about 75 to about 35, about 75 to about 45, about 75 to about 55, about 75 to about 65, about 65 to about 25, about 65 to about 35, about 65 to about 45, about 65 to about 55, about 55 to about 25, about 55 to about 35, about 55 to about 45, about 45 to about 25, about 45 to about 35, or about 35 to about 25 weight percent hydrogen fluoride and from about 20 to about 75 weight percent (Z)-1,2-dichloro-1,1,4,4,4-pentafluorobut-2-ene, for example, about 20 to about 65, about 20 to about 55, about 20 to about 45, about 20 to about 35, about 20 to about 25, about 25 to about 75, about 25 to about 65, about 25 to about 55, about 25 to about 45, about 25 to about 35, about 35 to about 75, about 35 to about 65, about 35 to about 55, about 35 to about 45, about 45 to about 75, about 45 to about 65, about 45 to about 55, about 55 to about 75, about 55 to about 65, or about 65 to about 75 weight percent (Z)-1,2-dichloro-1,1,4,4,4-pentafluorobut-2-ene.

In some embodiments, the compositions comprising hydrogen fluoride and (Z)-1,2-dichloro-1,1,4,4,4-pentafluorobut-2-ene have a boiling point of from about −25° C. to about 145° C., for example, about −25° C. to about 140° C., about −25° C. to about 125° C., about −25° C. to about 100° C., about −25° C. to about 50° C., about −25° C. to about 25° C., about −25° C. to about 0° C., about −25° C. to about −20° C., about −20° C. to about 145° C., about −20° C. to about 140° C., about −20° C. to about 125° C., about −20° C. to about 100° C., about −20° C. to about 50° C., about −20° C. to about 25° C., about −20° C. to about 0° C., about 0° C. to about 145° C., about 0° C. to about 140° C., about 0° C. to about 125° C., about 0° C. to about 100° C., about 0° C. to about 50° C., about 0° C. to about 25° C., about 20° C. to about 145° C., about 20° C. to about 140° C., about 20° C. to about 125° C., about 20° C. to about 100° C., about 20° C. to about 50° C., about 50° C. to about 145° C., about 50° C. to about 140° C., about 50° C. to about 125° C., about 50° C. to about 100° C., about 100° C. to about 145° C., about 100° C. to about 140° C., about 100° C. to about 125° C., about 125° C. to about 145° C., about 125° C. to about 140° C., or about 125° C. to about 145° C. at a pressure of from about 1 psia to about 500 psia, for example, about 1 psia to about 400 psia, about 1 psia to about 300 psia, about 1 psia to about 200 psia, about 1 psia to about 100 psia, about 1 psia to about 50 psia, about 1 psia to about 25 psia, about 25 psia to about 500 psia, about 25 psia to about 400 psia, about 25 psia to about 300 psia, about 25 psia to about 200 psia, about 25 psia to about 100 psia, about 25 psia to about 50 psia, about 50 psia to about 500 psia, about 50 psia to about 400 psia, about 50 psia to about 300 psia, about 50 psia to about 200 psia, about 50 psia to about 100 psia, about 100 psia to about 500 psia, about 100 psia to about 400 psia, about 100 psia to about 300 psia, about 100 psia to about 200 psia, about 200 psia to about 500 psia, about 200 psia to about 400 psia, about 200 psia to about 300 psia, about 300 psia to about 500 psia, about 300 psia to about 400 psia, or about 400 psia to about 500 psia.

In some embodiments, the compound of Formula I is 1,1,1,2,4,4,4-heptafluorobut-2-ene, wherein the 1,1,1,2,4,4,4-heptafluorobut-2-ene is present in an amount effective to form an azeotrope or an azeotrope-like composition with the hydrogen fluoride.

In some embodiments, the compositions comprise from about 55 to about 75 mole percent hydrogen fluoride, for example, about 55 to about 70, about 55 to about 65, about 55 to about 60, about 60 to about 75, about 60 to about 70, about 60 to about 65, about 65 to about 75, about 65 to about 70, or about 70 to about 75 mole percent hydrogen fluoride and from about 45 to about 25 mole percent 1,1,1,2,4,4,4-heptafluorobut-2-ene, for example, about 45 to about 30, about 45 to about 35, about 45 to about 40, about 40 to about 25, about 40 to about 30, about 40 to about 35, about 35 to about 25, about 35 to about 30, or about 30 to about 25 mole percent 1,1,1,2,4,4,4-heptafluorobut-2-ene.

In some embodiments, the compositions comprise from about 10 to about 25 weight percent hydrogen fluoride, for example, about 10 to about 20, about 10 to about 15, about 15 to about 25, about 15 to about 20, about 20 to about 25 weight percent hydrogen fluoride and from about 90 to about 75 weight percent 1,1,1,2,4,4,4-heptafluorobut-2-ene, for example, about 90 to about 80, about 90 to about 85, about 85 to about 75, about 85 to about 80, or about 80 to about 75 weight percent 1,1,1,2,4,4,4-heptafluorobut-2-ene.

In some embodiments, the compositions comprising hydrogen fluoride and 1,1,1,2,4,4,4-heptafluorobut-2-ene have a boiling point of from about −40° C. to about 125° C., for example, about −40° C. to about 100° C., about −40° C. to about 75° C., about −40° C. to about 50° C., about −40° C. to about 25° C., about −40° C. to about 0° C., about −40° C. to about −25° C., about −25° C. to about 125° C., about −25° C. to about 100° C., about −25° C. to about 75° C., about −25° C. to about 50° C., about −25° C. to about 25° C., about −25° C. to about 0° C., about 0° C. to about 125° C., about 0° C. to about 100° C., about 0° C. to about 75° C., about 0° C. to about 50° C., about 0° C. to about 25° C., about 25° C. to about 125° C., about 25° C. to about 100° C., about 25° C. to about 75° C., about 25° C. to about 50° C., about 50° C. to about 125° C., about 50° C. to about 100° C., about 50° C. to about 75° C., about 75° C. to about 125° C., about 75° C. to about 100° C., or about 100° C. to about 125° C. at a pressure of from about 1 psia to about 1000 psia, for example, about 1 psia to about 800 psia, about 1 psia to about 600 psia, about 1 psia to about 400 psia, about 1 psia to about 200 psia, about 1 psia to about 100 psia, about 1 psia to about 50 psia, about 50 psia to about 1000 psia, about 50 psia to about 800 psia, about 50 psia to about 600 psia, about 50 psia to about 400 psia, about 50 psia to about 200 psia, about 50 psia to about 100 psia, about 100 psia to about 1000 psia, about 100 psia to about 800 psia, about 100 psia to about 600 psia, about 100 psia to about 400 psia, about 100 psia to about 200 psia, about 200 psia to about 1000 psia, about 200 psia to about 800 psia, about 200 psia to about 600 psia, about 200 psia to about 400 psia, about 400 psia to about 1000 psia, about 400 psia to about 800 psia, about 400 psia to about 600 psia, about 600 psia to about 1000 psia, about 600 psia to about 800 psia, or about 800 psia to about 1000 psia.

In some embodiments, the compositions provided herein comprise:

from about 75 to about 99 mole percent hydrogen fluoride and from about 25 to about 1 mole percent (E)-2,3-dichlorohexafluoro-2-butene, wherein the composition has a boiling point of from about 0° C. to about 130° C. at a pressure of from about 5 psia to about 1000 psia; or from about 75 to about 99 mole percent hydrogen fluoride and from about 25 to about 1 mole percent (Z)-2,3-dichlorohexafluoro-2-butene, wherein the composition has a boiling point of from about 0° C. to about 130° C. at a pressure of from about 5 psia to about 1000 psia; or from about 75 to about 99 mole percent hydrogen fluoride and from about 25 to about 1 mole percent 2,3-dichlorohexafluoro-2-butene, wherein the composition has a boiling point of from about 0° C. to about 130° C. at a pressure of from about 5 psia to about 1100 psia; or from about 60 to about 99 mole percent hydrogen fluoride and from about 40 to about 1 mole percent (E)-2-chloro-1,1,1,4,4,4-hexafluoro-2-butene, wherein the composition has a boiling point of from about −25° C. to about 145° C. at a pressure of from about 1 psia to about 800 psia; or from about 65 to about 95 mole percent hydrogen fluoride and from about 35 to about 5 mole percent (Z)-2-chloro-1, 1,1,4,4,4-hexafluoro-2-butene, wherein the composition has a boiling point of from about −25° C. to about 145° C. at a pressure of from about 1 psia to about 850 psia; or from about 75 to about 99 mole percent hydrogen fluoride and from about 25 to about 1 mole percent dl-2,3-dichloro-1,1,1,4,4,4-hexafluorobutane, wherein the composition has a boiling point of from about 0° C. to about 140° C. at a pressure of from about 5 psia to about 1000 psia; or from about 75 to about 99 mole percent hydrogen fluoride and from about 25 to about 1 mole percent meso-2,3-dichloro-1,1,1,4,4,4-hexafluorobutane, wherein the composition has a boiling point of from about 0° C. to about 140° C. at a pressure of from about 5 psia to about 1000 psia; or from about 60 to about 90 mole percent hydrogen fluoride and from about 40 to about 10 mole percent 2-chloro-1,1,1,3,4,4,4-heptafluorobut-2-ene, wherein the composition has a boiling point of from about −25° C. to about 145° C. at a pressure of from about 1 psia to about 850 psia; or from about 60 to about 95 mole percent hydrogen fluoride and from about 40 to about 5 mole percent 2-chloro-1,1,1,2,4,4,4-heptafluorobutane, wherein the composition has a boiling point of from about −25° C. to about 145° C. at a pressure of from about 1 psia to about 800 psia; or from about 80 to about 99 mole percent hydrogen fluoride and from about 20 to about 1 mole percent (Z)-1,2-dichloro-1,1,4,4,4-pentafluorobut-2-ene, wherein the composition has a boiling point of from about −25° C. to about 145° C. at a pressure of from about 1 psia to about 500 psia; or from about 55 to about 75 mole percent hydrogen fluoride and from about 45 to about 25 mole percent 1,1,1,2,4,4,4-heptafluorobut-2-ene, wherein the composition has a boiling point of from about −40° C. to about 125° C. at a pressure of from about 1 psia to about 1000 psia.

In some embodiments, the compositions provided herein comprise:

from about 20 to about 75 weight percent hydrogen fluoride and from about 80 to about 25 weight percent (E)-2,3-dichlorohexafluoro-2-butene, wherein the composition has a boiling point of from about 0° C. to about 130° C. at a pressure of from about 5 psia to about 1000 psia; or from about 20 to about 75 weight percent hydrogen fluoride and from about 80 to about 25 weight percent (Z)-2,3-dichlorohexafluoro-2-butene, wherein the composition has a boiling point of from about 0° C. to about 130° C. at a pressure of from about 5 psia to about 1000 psia; or from about 20 to about 75 weight percent hydrogen fluoride and from about 80 to about 25 weight percent 2,3-dichlorohexafluoro-2-butene, wherein the composition has a boiling point of from about 0° C. to about 130° C. at a pressure of from about 5 psia to about 1100 psia; or from about 15 to about 60 weight percent hydrogen fluoride and from about 85 to about 40 weight percent (E)-2-chloro-1,1,1,4,4,4-hexafluoro-2-butene, wherein the composition has a boiling point of from about −25° C. to about 145° C. at a pressure of from about 1 psia to about 800 psia; or from about 15 to about 50 weight percent hydrogen fluoride and from about 85 to about 50 weight percent (Z)-2-chloro-1,1,1,4,4,4-hexafluoro-2-butene, wherein the composition has a boiling point of from about −25° C. to about 145° C. at a pressure of from about 1 psia to about 850 psia; or from about 20 to about 75 weight percent hydrogen fluoride and from about 80 to about 25 weight percent dl-2,3-dichloro-1,1,1,4,4,4-hexafluorobutane, wherein the composition has a boiling point of from about 0° C. to about 140° C. at a pressure of from about 5 psia to about 1000 psia; or from about 20 to about 85 weight percent hydrogen fluoride and from about 80 to about 15 weight percent meso-2,3-dichloro-1,1,1,4,4,4-hexafluorobutane, wherein the composition has a boiling point of from about 0° C. to about 140° C. at a pressure of from about 5 psia to about 1000 psia; or from about 10 to about 45 weight percent hydrogen fluoride and from about 90 to about 55 weight percent 2-chloro-1,1,1,3,4,4,4-heptafluorobut-2-ene, wherein the composition has a boiling point of from about −25° C. to about 140° C. at a pressure of from about 1 psia to about 850 psia; or from about 60 to about 10 weight percent hydrogen fluoride and from about 40 to about 90 weight percent 2-chloro-1,1,1,2,4,4,4-heptafluorobutane, wherein the composition has a boiling point of from about −25° C. to about 145° C. at a pressure of from about 1 psia to about 800 psia;

from about 80 to about 25 weight percent hydrogen fluoride and from about 20 to about 75 weight percent (Z)-1,2-dichloro-1,1,4,4,4-pentafluorobut-2-ene, wherein the composition has a boiling point of from about −25° C. to about 145° C. at a pressure of from about 1 psia to about 500 psia;

from about 10 to about 25 weight percent hydrogen fluoride and from about 90 to about 75 weight percent 1,1,1,2,4,4,4-heptafluorobut-2-ene, wherein the composition has a boiling point of from about −40° C. to about 125° C. at a pressure of from about 1 psia to about 1000 psia.

In some embodiments, the compositions provided herein comprise:

from about 74.0 to about 96.6 mole percent hydrogen fluoride and from about 3.4 to about 26.0 mole percent (E)-2,3-dichlorohexafluoro-2-butene, wherein the composition has a boiling point of from about 0° C. to about 130° C. at a pressure of from about 7.8 psia to about 994.5 psia; or from about 74.3 to about 97.0 mole percent hydrogen fluoride and from about 3.0 to about 25.7 mole percent (Z)-2,3-dichlorohexafluoro-2-butene, wherein the composition has a boiling point of from about 0° C. to about 130° C. at a pressure of from about 7.6 psia to about 968.1 psia; or from about 74.7 to about 96.8 mole percent hydrogen fluoride and from about 3.2 to about 25.3 mole percent 2,3-dichlorohexafluoro-2-butene, wherein the composition has a boiling point of from about 0° C. to about 130° C. at a pressure of from about 7.7 psia to about 1068.5 psia; or from about 93.5 to about 66.0 mole percent hydrogen fluoride and from about 6.5 to about 34.0 mole percent E-2-chloro-1,1,1,4,4,4-hexafluoro-2-butene, wherein the composition has a boiling point of from about −20° C. to about 140° C. at a pressure of from about 3.5 psia to about 775 psia; or from about 90.9 to about 65.0 mole percent hydrogen fluoride and from about 9.1 to about 35.0 mole percent Z-2-chloro-1,1,1,4,4,4-hexafluoro-2-butene, wherein the composition has a boiling point of from about −20° C. to about 140° C. at a pressure of from about 3.8 psia to about 833.8 psia; or from about 97.1 to about 76.8 mole percent hydrogen fluoride and from about 2.9 to about 23.2 mole percent dl-2,3-dichloro-1,1,1,4,4,4-hexafluorobutane, wherein the composition has a boiling point of from about 0° C. to about 140° C. at a pressure of from about 7.4 psia to about 1045.3 psia; or from about 98.2 to about 77.6 mole percent hydrogen fluoride and from about 1.8 to about 22.4 mole percent meso-2,3-dichloro-1,1,1,4,4,4-hexafluorobutane, wherein the composition has a boiling point of from about 0° C. to about 140° C. at a pressure of from about 7.2 psia to about 984.6 psia; or from about 89.3 to about 62.1 mole percent hydrogen fluoride and from about 10.7 to about 37.9 mole percent 2-chloro-1,1,1,3,4,4,4-heptafluorobut-2-ene, wherein the composition has a boiling point of from about −20° C. to about 130° C. at a pressure of from about 4.2 psia to about 852.0 psia; or from about 93.9 to about 62.0 mole percent hydrogen fluoride and from about 6.1 to about 38.0 mole percent 2-chloro-1,1,1,2,4,4,4-heptafluorobutane, wherein the composition has a boiling point of from about −20° C. to about 140° C. at a pressure of from about 3.3 psia to about 791.8 psia; or from about 97.8 to about 81.6 mole percent hydrogen fluoride and from about 2.2 to about 18.4 mole percent Z-1,2-dichloro-1,1,4,4,4-pentafluorobut-2-ene, wherein the composition has a boiling point of from about −20° C. to about 140° C. at a pressure of from about 3.0 psia to about 481.0 psia; or from about 74.5 to about 55.6 mole percent hydrogen fluoride and from about 25.5 to about 44.4 mole percent 1,1,1,2,4,4,4-heptafluorobut-2-ene, wherein the composition has a boiling point of from about −40° C. to about 125° C. at a pressure of from about 2.3 psia to about 1042.0 psia.

The present application further provides a composition comprising:
  i) hydrogen fluoride; and
  ii) a compound selected from the group consisting of:
    2,3-dichlorohexafluoro-2-butene;
    2-chloro-1,1,1,4,4,4-hexafluoro-2-butene;
    2,3-dichloro-1,1,1,4,4,4-hexafluorobutane;
    2-chloro-1,1,1,3,4,4,4-heptafluorobut-2-ene;
    1,1,1,2,4,4,4-heptafluorobut-2-ene;
    2-chloro-1,1,1,2,4,4,4-heptafluorobutane;
    1,2-dichloro-1,1,4,4,4-pentafluorobut-2-ene;
    1,2-dichloro-1,1,2,2-tetrafluoroethane;
    2-chloro-1,1,1,3,4,4,4-heptafluorobutane;
    2-chloro-1,1,1,3,3-pentafluoropropane;
    1,2-dichloro-1,1,2-trifluoroethane;
    2,2-dichloro-1,1,1,4,4,4-hexafluorobutane;
    1,2-dichloro-1,1,2,4,4,4-hexafluorobutane;
    1,2-dichloro-3,3,4,4,4-pentafluorobut-1-ene;
    2,3-dichloro-1,1,1,3-tetrafluoropropane;
    1,2,3-trichloro-1,1,4,4,4-pentafluorobutane;
    1,2,2-trichloro-1,1-difluoroethane;
    1,1,2,2-tetrachloro-1,2-difluoroethane;
    1,1,1,2-tetrachloro-2,2-difluoroethane;
    1,2-dichloro-3,3,4,4-tetrafluorocyclobut-1-ene; and
    1,1,2,3-tetrachloro-4,4,4-trifluorobut-1-ene;
  wherein the compound is present in an amount effective to form an azeotrope composition or an azeotrope-like composition with the hydrogen fluoride.

The present application further provides a composition comprising:
  i) hydrogen fluoride; and
  ii) a compound selected from the group consisting of:
    2,3-dichlorohexafluoro-2-butene;
    (E)-2,3-dichlorohexafluoro-2-butene;
    (Z)-2,3-dichlorohexafluoro-2-butene;
    (E)-2-chloro-1,1,1,4,4,4-hexafluoro-2-butene;
    (Z)-2-chloro-1,1,1,4,4,4-hexafluoro-2-butene;
    (d1)-2,3-dichloro-1,1,1,4,4,4-hexafluorobutane;
    meso-2,3-dichloro-1,1,1,4,4,4-hexafluorobutane;
    2-chloro-1,1,1,3,4,4,4-heptafluorobut-2-ene;
    1,1,1,2,4,4,4-heptafluorobut-2-ene;
    2-chloro-1,1,1,2,4,4,4-heptafluorobutane;
    (E)-1,2-dichloro-1,1,4,4,4-pentafluorobut-2-ene;
    (Z)-1,2-dichloro-1,1,4,4,4-pentafluorobut-2-ene;
    1,2-dichloro-1,1,2,2-tetrafluoroethane;
    2-chloro-1,1,1,3,4,4,4-heptafluorobutane;
    2-chloro-1,1,1,3,3-pentafluoropropane;
    1,2-dichloro-1,1,2-trifluoroethane;
    2,2-dichloro-1,1,1,4,4,4-hexafluorobutane;
    1,2-dichloro-1,1,2,4,4,4-hexafluorobutane;
    (E)-1,2-dichloro-3,3,4,4,4-pentafluorobut-1-ene;
    (Z)-1,2-dichloro-3,3,4,4,4-pentafluorobut-1-ene;
    2,3-dichloro-1,1,1,3-tetrafluoropropane;
    1,2,3-trichloro-1,1,4,4,4-pentafluorobutane;
    1,2,2-trichloro-1,1-difluoroethane;
    1,1,2,2-tetrachloro-1,2-difluoroethane;
    1,1,1,2-tetrachloro-2,2-difluoroethane;
    1,2-dichloro-3,3,4,4-tetrafluorocyclobut-1-ene; and
    1,1,2,3-tetrachloro-4,4,4-trifluorobut-1-ene;
  wherein the compound is present in an amount effective to form an azeotrope composition or an azeotrope-like composition with the hydrogen fluoride.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. Vapor-Liquid Equilibrium Analysis

The PTx method is a known method for experimentally measuring vapor-liquid phase equilibrium (VLE) data of a mixture. The measurements can be made either isothermally or isobarically. The isothermal method requires measurement of the total pressure of mixtures of known composition at constant temperature. In this method, the total absolute pressure in a cell of known volume is measured at a constant temperature for various known compositions of the two compounds. The isobaric method requires measurement of the temperature of mixtures of known composition at constant pressure. In this method, the temperature in a cell of known volume is measured at a constant pressure for various known compositions of the two compounds. Use of the PTx Method is described in detail in "Phase Equilibrium in Process Design", Wiley-Interscience Publisher, 1970, written by Harold R. Null, on pages 124 to 126, the disclosure of which is incorporated herein by reference in its entirety.

The measured data points can be converted into equilibrium vapor and liquid compositions in the PTx cell by using an activity coefficient equation model, such as the Non-Random, Two-Liquid (NRTL) equation, to represent liquid phase nonidealities. Use of an activity coefficient equation, such as the NRTL equation is described in detail in "The Properties of Gases and Liquids," 4th edition, published by McGraw Hill, written by Reid, Prausnitz and Poling, on pages 241 to 387, and in "Phase Equilibria in Chemical Engineering," published by Butterworth Publishers, 1985, written by Stanley M. Walas, pages 165 to 244, the disclosure of which is incorporated herein by reference in its entirety. Without wishing to be bound by any theory or explanation, it is believed that the NRTL equation, together with the PTx cell data, sufficiently predicts the vapor-liquid phase equilibrium behavior of the various mixture compositions of the present invention and as well as the behavior of these mixtures in multi-stage separation equipment such as distillation columns.

Example 2. Azeotropic Compositions of Hydrogen Fluoride and E-1316mxx

Experimental PTx phase equilibrium data for HF and E-CFC-1316mxx was measured at 29.67 & 79.29° C. The data was fit using the NRTL (non-random two-liquid) activity coefficient model and the resulting parameters used for modeling the mixture phase equilibrium. At a constant 29.67° C., the concentrations of E-1316mxx & HF in the mixture were varied in small increments and the corresponding equilibrium pressure was calculated at each liquid composition. Table 1 shows representative calculated points starting from pure E-1316mxx and slowly adding HF. Table 2 shows selected calculated points starting from pure HF and slowly adding E-1316mxx.

TABLE 1

| HF (mole %) | E-1316mxx (mole %) | Pressure (psia) |
|---|---|---|
| 0.00% | 100.00% | 3.65 |
| 1.00% | 99.00% | 8.35 |
| 2.00% | 98.00% | 11.89 |
| 3.00% | 97.00% | 15.17 |
| 4.00% | 96.00% | 18.51 |
| 5.00% | 95.00% | 21.61 |
| 6.00% | 94.00% | 24.13 |
| 6.17% | 93.83% | 24.48 |
| 7.00% | 93.00% | 24.48 |
| 8.00% | 92.00% | 24.48 |
| 10.00% | 90.00% | 24.48 |
| 20.00% | 80.00% | 24.48 |
| 30.00% | 70.00% | 24.48 |
| 40.00% | 60.00% | 24.48 |
| 50.00% | 50.00% | 24.48 |

TABLE 2

| HF (mole %) | E-1316mxx (mole %) | Pressure (psia) |
|---|---|---|
| 100.00% | 0.00% | 21.06 |
| 99.00% | 1.00% | 24.35 |
| 98.94% | 1.06% | 24.47 |
| 98.00% | 2.00% | 24.48 |
| 97.00% | 3.00% | 24.48 |
| 96.00% | 4.00% | 24.48 |
| 95.00% | 5.00% | 24.48 |
| 90.00% | 10.00% | 24.48 |
| 85.00% | 15.00% | 24.48 |
| 80.00% | 20.00% | 24.48 |
| 75.00% | 25.00% | 24.48 |
| 70.00% | 30.00% | 24.48 |
| 60.00% | 40.00% | 24.48 |
| 55.00% | 45.00% | 24.48 |
| 50.00% | 50.00% | 24.48 |

Tables 1 and 2 clearly show that, starting from both pure HF and pure E-1316mxx, the equilibrium pressure increased until it reached a maximum pressure of 24.48 psia and that, once reached, the 24.48 psia pressure continued to exist over a wide composition range. The existence of a pressure maximum in the mixture vapor-liquid phase equilibrium at constant temperature indicated that a maximum-pressure or, equivalently, a minimum-boiling azeotrope exists. The existence of the maximum equilibrium pressure (at constant temperature) over a wide composition range indicated that the azeotrope is heterogeneous. As confirmation, the presence of two liquid phases was visually observed during the phase equilibrium experiments. Based on Tables 1 & 2, at 29.67° C., azeotropic and/or azeotrope-like behavior exists from approximately 6.17 to 98.94 mole percent HF (93.83 to 1.06 mole percent E-1316mxx), where the equilibrium pressure is about 24.48 psia.

The calculations described above were repeated at various temperatures for both the same and the other mixtures of the present invention with the results for each mixture summarized in the Examples and Tables 3A-14. The calculated azeotropic and azeotrope-like ranges for the HF/E-1316mxx mixture from 0° C. to 130° C. are summarized in Tables 3A-3B.

TABLE 3A

HF/E-1316mxx Heterogeneous Azeotrope

| Azeotropic Temp (° C.) | Azeotropic Pressure (psia) | Vapor-Phase Composition (mole percent) | | Liquid 1 Composition (mole percent) | | Liquid 2 Composition (mole percent) | |
|---|---|---|---|---|---|---|---|
| | | HF | E-1316mxx | HF | E-1316mxx | HF | E-1316mxx |
| 0 | 7.75 | 96.64 | 3.36 | 99.43 | 0.57 | 3.10 | 96.90 |
| 10 | 11.70 | 95.96 | 4.04 | 99.29 | 0.71 | 3.96 | 96.04 |
| 20 | 17.22 | 95.19 | 4.81 | 99.12 | 0.88 | 4.99 | 95.01 |
| 29.67 | 24.44 | 94.34 | 5.66 | 98.93 | 1.07 | 6.17 | 93.83 |
| 30 | 24.77 | 94.31 | 5.69 | 98.93 | 1.07 | 6.21 | 93.79 |
| 40 | 34.91 | 93.31 | 6.69 | 98.70 | 1.30 | 7.62 | 92.38 |
| 50 | 48.37 | 92.17 | 7.83 | 98.43 | 1.57 | 9.20 | 90.80 |
| 60 | 66.04 | 90.88 | 9.12 | 98.12 | 1.88 | 10.91 | 89.09 |
| 70 | 89.05 | 89.39 | 10.61 | 97.76 | 2.24 | 12.71 | 87.29 |
| 79.29 | 116.61 | 87.78 | 12.22 | 97.37 | 2.63 | 14.44 | 85.56 |
| 80 | 119.01 | 87.65 | 12.35 | 97.34 | 2.66 | 14.58 | 85.42 |
| 90 | 158.30 | 85.52 | 14.48 | 96.85 | 3.15 | 16.52 | 83.48 |
| 100 | 211.50 | 82.51 | 17.49 | 96.29 | 3.71 | 18.54 | 81.46 |
| 110 | 562.72 | 73.96 | 26.04 | 95.63 | 4.37 | 20.67 | 79.33 |
| 120 | 778.62 | 74.95 | 25.05 | 94.85 | 5.15 | 22.95 | 77.05 |
| 130 | 994.46 | 75.85 | 24.15 | 93.94 | 6.06 | 25.40 | 74.60 |

TABLE 3B

HF/E-1316mxx Heterogeneous Azeotrope

| Azeotropic Temperature (° C.) | Azeotropic Pressure (psia) | Vapor-Phase Composition (mass percent) | | Liquid 1 Composition (mass percent) | | Liquid 2 Composition (mass percent) | |
|---|---|---|---|---|---|---|---|
| | | HF | E-1316mxx | HF | E-1316mxx | HF | E-1316mxx |
| 0 | 7.75 | 71.18 | 28.82 | 93.76 | 6.24 | 0.27 | 99.73 |
| 10 | 11.70 | 67.12 | 32.88 | 92.32 | 7.68 | 0.35 | 99.65 |
| 20 | 17.22 | 62.96 | 37.04 | 90.66 | 9.34 | 0.45 | 99.55 |
| 29.67 | 24.44 | 58.88 | 41.12 | 88.85 | 11.15 | 0.56 | 99.44 |
| 30 | 24.77 | 58.74 | 41.26 | 88.79 | 11.21 | 0.57 | 99.43 |
| 40 | 34.91 | 54.51 | 45.49 | 86.68 | 13.32 | 0.70 | 99.30 |
| 50 | 48.37 | 50.29 | 49.71 | 84.34 | 15.66 | 0.86 | 99.14 |
| 60 | 66.04 | 46.11 | 53.89 | 81.76 | 18.24 | 1.04 | 98.96 |
| 70 | 89.05 | 41.98 | 58.02 | 78.94 | 21.06 | 1.24 | 98.76 |
| 79.29 | 116.61 | 38.16 | 61.84 | 76.09 | 23.91 | 1.43 | 98.57 |
| 80 | 119.01 | 37.87 | 62.13 | 75.87 | 24.13 | 1.44 | 98.56 |
| 90 | 158.30 | 33.66 | 66.34 | 72.56 | 27.44 | 1.67 | 98.33 |
| 100 | 211.50 | 28.84 | 71.16 | 69.02 | 30.98 | 1.92 | 98.08 |
| 110 | 562.72 | 19.61 | 80.39 | 65.25 | 34.75 | 2.19 | 97.81 |
| 120 | 778.62 | 20.45 | 79.55 | 61.28 | 38.72 | 2.49 | 97.51 |
| 130 | 994.46 | 21.24 | 78.76 | 57.11 | 42.89 | 2.84 | 97.16 |

Example 3. Azeotropic Compositions of Hydrogen Fluoride and Z-1316Mxx

The calculated azeotropic and azeotrope-like ranges for HF/Z-1316mxx mixtures from 0° C. to 130° C. are summarized in Tables 4A-4B.

TABLE 4A

HF/Z-1316mxx Heterogeneous Azeotrope

| Azeotropic Temperature (° C.) | Azeotropic Pressure (psia) | Vapor-Phase Composition (mole percent) | | Liquid 1 Composition (mole percent) | | Liquid 2 Composition (mole percent) | |
|---|---|---|---|---|---|---|---|
| | | HF | Z-1316mxx | HF | Z-1316mxx | HF | Z-1316mxx |
| 0 | 7.65 | 97.00 | 3.00 | 99.43 | 0.57 | 3.10 | 96.90 |
| 10 | 11.54 | 96.37 | 3.63 | 99.29 | 0.71 | 3.96 | 96.04 |
| 20 | 16.97 | 95.65 | 4.35 | 99.12 | 0.88 | 4.99 | 95.01 |
| 30 | 24.38 | 94.82 | 5.18 | 98.93 | 1.07 | 6.21 | 93.79 |
| 40 | 34.34 | 93.87 | 6.13 | 98.70 | 1.30 | 7.62 | 92.38 |
| 50 | 47.54 | 92.80 | 7.20 | 98.43 | 1.57 | 9.20 | 90.80 |
| 60 | 64.84 | 91.56 | 8.44 | 98.12 | 1.88 | 10.91 | 89.09 |
| 70 | 87.35 | 90.14 | 9.86 | 97.76 | 2.24 | 12.71 | 87.29 |
| 80 | 116.58 | 88.48 | 11.52 | 97.34 | 2.66 | 14.58 | 85.42 |
| 90 | 154.77 | 86.46 | 13.54 | 96.85 | 3.15 | 16.52 | 83.48 |
| 100 | 205.98 | 83.69 | 16.31 | 96.29 | 3.71 | 18.54 | 81.46 |
| 110 | 536.50 | 74.32 | 25.68 | 95.63 | 4.37 | 20.67 | 79.33 |
| 120 | 752.39 | 75.31 | 24.69 | 94.85 | 5.15 | 22.95 | 77.05 |
| 130 | 968.09 | 76.20 | 23.80 | 93.94 | 6.06 | 25.40 | 74.60 |

TABLE 4B

HF/Z-1316mxx Heterogeneous Azeotrope

| Azeotropic Temperature (° C.) | Azeotropic Pressure (psia) | Vapor-Phase Composition (mass percent) | | Liquid 1 Composition (mass percent) | | Liquid 2 Composition (mass percent) | |
|---|---|---|---|---|---|---|---|
| | | HF | Z-1316mxx | HF | Z-1316mxx | HF | Z-1316mxx |
| 0 | 7.65 | 73.50 | 26.50 | 93.76 | 6.24 | 0.27 | 99.73 |
| 10 | 11.54 | 69.50 | 30.50 | 92.32 | 7.68 | 0.35 | 99.65 |
| 20 | 16.97 | 65.35 | 34.65 | 90.66 | 9.34 | 0.45 | 99.55 |
| 30 | 24.38 | 61.12 | 38.88 | 88.79 | 11.21 | 0.57 | 99.43 |
| 40 | 34.34 | 56.83 | 43.17 | 86.68 | 13.32 | 0.70 | 99.30 |
| 50 | 47.54 | 52.53 | 47.47 | 84.34 | 15.66 | 0.86 | 99.14 |
| 60 | 64.84 | 48.24 | 51.76 | 81.76 | 18.24 | 1.04 | 98.96 |

TABLE 4B-continued

HF/Z-1316mxx Heterogeneous Azeotrope

| Azeotropic Temperature (° C.) | Azeotropic Pressure (psia) | Vapor-Phase Composition (mass percent) | | Liquid 1 Composition (mass percent) | | Liquid 2 Composition (mass percent) | |
|---|---|---|---|---|---|---|---|
| | | HF | Z-1316mxx | HF | Z-1316mxx | HF | Z-1316mxx |
| 70 | 87.35 | 43.99 | 56.01 | 78.94 | 21.06 | 1.24 | 98.76 |
| 80 | 116.58 | 39.75 | 60.25 | 75.87 | 24.13 | 1.44 | 98.56 |
| 90 | 154.77 | 35.42 | 64.58 | 72.56 | 27.44 | 1.67 | 98.33 |
| 100 | 205.98 | 30.59 | 69.41 | 69.02 | 30.98 | 1.92 | 98.08 |
| 110 | 536.50 | 19.91 | 80.09 | 65.25 | 34.75 | 2.19 | 97.81 |
| 120 | 752.39 | 20.76 | 79.24 | 61.28 | 38.72 | 2.49 | 97.51 |
| 130 | 968.09 | 21.57 | 78.43 | 57.11 | 42.89 | 2.84 | 97.16 |

Example 4. Azeotropic Composition of Hydrogen Fluoride and 1316Mxx (Mixture of Z-/E-Isomers)

The calculated azeotropic and azeotrope-like ranges for HF/1316mxx mixtures (45:55 mol % Z:E isomers) from 0° C. to 130° C. are summarized in Tables 5A-5B.

Example 5. Azeotropic Compositions of Hydrogen Fluoride and E-1326mxz

The calculated azeotropic and azeotrope-like ranges for HF/E-1326mxz mixtures from −20° C. to 140° C. are summarized in Tables 6A-6B.

TABLE 5A

| Azeotropic Temperature (° C.) | Azeotropic Pressure (psia) | Vapor-Phase Composition (mole percent) | | Liquid 1 Composition (mole percent) | | Liquid Composition (mole percent) | |
|---|---|---|---|---|---|---|---|
| | | HF | Z/E-1316mxx | HF | Z/E-1316mxx | HF | Z/E-1316mxx |
| 0 | 7.70 | 96.82 | 3.18 | 99.43 | 0.57 | 3.10 | 96.90 |
| 10 | 11.62 | 96.17 | 3.83 | 99.29 | 0.71 | 3.96 | 96.04 |
| 20 | 17.09 | 95.44 | 4.56 | 99.12 | 0.88 | 4.99 | 95.01 |
| 30 | 24.55 | 94.60 | 5.40 | 98.93 | 1.07 | 6.21 | 93.79 |
| 40 | 34.57 | 93.66 | 6.34 | 98.70 | 1.30 | 7.62 | 92.38 |
| 50 | 47.84 | 92.60 | 7.40 | 98.43 | 1.57 | 9.20 | 90.80 |
| 60 | 65.19 | 91.40 | 8.60 | 98.12 | 1.88 | 10.91 | 89.09 |
| 70 | 87.70 | 90.05 | 9.95 | 97.76 | 2.24 | 12.71 | 87.29 |
| 80 | 116.79 | 88.52 | 11.48 | 97.34 | 2.66 | 14.58 | 85.42 |
| 90 | 154.48 | 86.74 | 13.26 | 96.85 | 3.15 | 16.52 | 83.48 |
| 100 | 204.02 | 84.54 | 15.46 | 96.29 | 3.71 | 18.54 | 81.46 |
| 110 | 273.02 | 81.00 | 19.00 | 95.63 | 4.37 | 20.67 | 79.33 |
| 120 | 807.53 | 74.67 | 25.33 | 94.85 | 5.15 | 22.95 | 77.05 |
| 130 | 1068.51 | 75.08 | 24.92 | 93.94 | 6.06 | 25.40 | 74.60 |

TABLE 5B

| Azeotropic Temperature (° C.) | Azeotropic Pressure (psia) | Vapor-Phase Composition (mass percent) | | Liquid 1 Composition (mass percent) | | Liquid 2 Composition (mass percent) | |
|---|---|---|---|---|---|---|---|
| | | HF | Z/E-1316mxx | HF | Z/E-1316mxx | HF | Z/E-1316mxx |
| 0 | 7.70 | 72.31 | 27.69 | 93.76 | 6.24 | 0.27 | 99.73 |
| 10 | 11.62 | 68.32 | 31.68 | 92.32 | 7.68 | 0.35 | 99.65 |
| 20 | 17.09 | 64.23 | 35.77 | 90.66 | 9.34 | 0.45 | 99.55 |
| 30 | 24.55 | 60.09 | 39.91 | 88.79 | 11.21 | 0.57 | 99.43 |
| 40 | 34.57 | 55.93 | 44.07 | 86.68 | 13.32 | 0.70 | 99.30 |
| 50 | 47.84 | 51.80 | 48.20 | 84.34 | 15.66 | 0.86 | 99.14 |
| 60 | 65.19 | 47.73 | 52.27 | 81.76 | 18.24 | 1.04 | 98.96 |
| 70 | 87.70 | 43.75 | 56.25 | 78.94 | 21.06 | 1.24 | 98.76 |
| 80 | 116.79 | 39.84 | 60.16 | 75.87 | 24.13 | 1.44 | 98.56 |
| 90 | 154.48 | 35.97 | 64.03 | 72.56 | 27.44 | 1.67 | 98.33 |
| 100 | 204.02 | 31.95 | 68.05 | 69.02 | 30.98 | 1.92 | 98.08 |
| 110 | 273.02 | 26.80 | 73.20 | 65.25 | 34.75 | 2.19 | 97.81 |
| 120 | 807.53 | 20.20 | 79.80 | 61.28 | 38.72 | 2.49 | 97.51 |
| 130 | 1068.51 | 20.56 | 79.44 | 57.11 | 42.89 | 2.84 | 97.16 |

TABLE 6A

| Azeotropic Temperature | Azeotropic Pressure | Vapor-Phase Composition (mole percent) | | Liquid 1 Composition (mole percent) | | Liquid 2 Composition (mole percent) | |
|---|---|---|---|---|---|---|---|
| (° C.) | (psia) | HF | E-1326mxz | HF | E-1326mxz | HF | E-1326mxz |
| −20 | 3.49 | 93.54 | 6.46 | 98.48 | 1.52 | 59.13 | 40.87 |
| −10 | 5.68 | 92.42 | 7.58 | 98.17 | 1.83 | 57.54 | 42.46 |
| 0 | 8.91 | 91.23 | 8.77 | 97.83 | 2.17 | 55.82 | 44.18 |
| 10 | 13.56 | 89.98 | 10.02 | 97.45 | 2.55 | 53.95 | 46.05 |
| 20 | 20.05 | 88.66 | 11.34 | 97.04 | 2.96 | 51.93 | 48.07 |
| 30 | 28.92 | 87.30 | 12.70 | 96.60 | 3.40 | 49.75 | 50.25 |
| 40 | 40.79 | 85.90 | 14.10 | 96.12 | 3.88 | 47.50 | 52.50 |
| 50 | 56.40 | 84.46 | 15.54 | 95.61 | 4.39 | 45.33 | 54.67 |
| 60 | 76.62 | 83.01 | 16.99 | 95.07 | 4.93 | 43.51 | 56.49 |
| 70 | 102.55 | 81.53 | 18.47 | 94.47 | 5.53 | 42.31 | 57.69 |
| 80 | 135.49 | 80.04 | 19.96 | 93.82 | 6.18 | 41.88 | 58.12 |
| 90 | 177.15 | 78.52 | 21.48 | 93.10 | 6.90 | 42.16 | 57.84 |
| 100 | 229.84 | 76.95 | 23.05 | 92.29 | 7.71 | 43.01 | 56.99 |
| 110 | 297.03 | 75.23 | 24.77 | 91.39 | 8.61 | 44.32 | 55.68 |
| 120 | 385.11 | 73.10 | 26.90 | 90.36 | 9.64 | 46.02 | 53.98 |
| 130 | 552.18 | 65.96 | 34.04 | 89.16 | 10.84 | 48.08 | 51.92 |
| 140 | 775.03 | 67.29 | 32.71 | 87.76 | 12.24 | 50.50 | 49.50 |

TABLE 6B

| Azeotropic Temperature | Azeotropic Pressure | Vapor-Phase Composition (mass percent) | | Liquid 1 Composition (mass percent) | | Liquid 2 Composition (mass percent) | |
|---|---|---|---|---|---|---|---|
| (° C.) | (psia) | HF | E-1326mxz | HF | E-1326mxz | HF | E-1326mxz |
| −20 | 3.49 | 59.35 | 40.65 | 86.71 | 13.29 | 12.73 | 87.27 |
| −10 | 5.68 | 55.14 | 44.86 | 84.38 | 15.62 | 12.02 | 87.98 |
| 0 | 8.91 | 51.19 | 48.81 | 81.93 | 18.07 | 11.30 | 88.70 |
| 10 | 13.56 | 47.50 | 52.50 | 79.39 | 20.61 | 10.56 | 89.44 |
| 20 | 20.05 | 44.08 | 55.92 | 76.77 | 23.23 | 9.82 | 90.18 |
| 30 | 28.92 | 40.93 | 59.07 | 74.11 | 25.89 | 9.08 | 90.92 |
| 40 | 40.79 | 38.04 | 61.96 | 71.43 | 28.57 | 8.36 | 91.64 |
| 50 | 56.40 | 35.40 | 64.60 | 68.73 | 31.27 | 7.71 | 92.29 |
| 60 | 76.62 | 32.99 | 67.01 | 66.01 | 33.99 | 7.20 | 92.80 |
| 70 | 102.55 | 30.79 | 69.21 | 63.26 | 36.74 | 6.88 | 93.12 |
| 80 | 135.49 | 28.78 | 71.22 | 60.47 | 39.53 | 6.77 | 93.23 |
| 90 | 177.15 | 26.92 | 73.08 | 57.61 | 42.39 | 6.84 | 93.16 |
| 100 | 229.84 | 25.17 | 74.83 | 54.69 | 45.31 | 7.07 | 92.93 |
| 110 | 297.03 | 23.44 | 76.56 | 51.68 | 48.32 | 7.43 | 92.57 |
| 120 | 385.11 | 21.50 | 78.50 | 48.57 | 51.43 | 7.91 | 92.09 |
| 130 | 552.18 | 16.34 | 83.66 | 45.34 | 54.66 | 8.54 | 91.46 |
| 140 | 775.03 | 17.17 | 82.83 | 41.95 | 58.05 | 9.33 | 90.67 |

Example 6. Azeotropic Compositions of Hydrogen Fluoride and Z-1326mxz

The calculated azeotropic and azeotrope-like ranges for HF/Z-1326mxz mixtures from −20° C. to 140° C. are summarized in Tables 7A-7B.

TABLE 7A

| Azeotropic Temperature | Azeotropic Pressure | Vapor-Phase Composition (mole percent) | | Liquid 1 Composition (mole percent) | | Liquid 2 Composition (mole percent) | |
|---|---|---|---|---|---|---|---|
| (° C.) | (psia) | HF | Z-1326mxz | HF | Z-1326mxz | HF | Z-1326mxz |
| −20 | 3.79 | 90.88 | 9.12 | 98.17 | 1.83 | 54.26 | 45.74 |
| −10 | 6.18 | 89.59 | 10.41 | 97.86 | 2.14 | 52.19 | 47.81 |
| 0 | 9.73 | 88.25 | 11.75 | 97.54 | 2.46 | 49.92 | 50.08 |
| 10 | 14.81 | 86.87 | 13.13 | 97.19 | 2.81 | 47.44 | 52.56 |
| 20 | 21.91 | 85.47 | 14.53 | 96.82 | 3.18 | 44.79 | 55.21 |
| 30 | 31.58 | 84.04 | 15.96 | 96.44 | 3.56 | 42.08 | 57.92 |
| 40 | 44.51 | 82.60 | 17.40 | 96.03 | 3.97 | 39.64 | 60.36 |

TABLE 7A-continued

| Azeotropic Temperature (° C.) | Azeotropic Pressure (psia) | Vapor-Phase Composition (mole percent) | | Liquid 1 Composition (mole percent) | | Liquid 2 Composition (mole percent) | |
|---|---|---|---|---|---|---|---|
| | | HF | Z-1326mxz | HF | Z-1326mxz | HF | Z-1326mxz |
| 50 | 61.47 | 81.15 | 18.85 | 95.59 | 4.41 | 37.89 | 62.11 |
| 60 | 83.41 | 79.70 | 20.30 | 95.13 | 4.87 | 37.01 | 62.99 |
| 70 | 111.49 | 78.26 | 21.74 | 94.63 | 5.37 | 36.91 | 63.09 |
| 80 | 147.11 | 76.84 | 23.16 | 94.10 | 5.90 | 37.38 | 62.62 |
| 90 | 192.10 | 75.42 | 24.58 | 93.51 | 6.49 | 38.24 | 61.76 |
| 100 | 248.95 | 73.99 | 26.01 | 92.87 | 7.13 | 39.39 | 60.61 |
| 110 | 321.43 | 72.47 | 27.53 | 92.18 | 7.82 | 40.76 | 59.24 |
| 120 | 416.52 | 70.64 | 29.36 | 91.41 | 8.59 | 42.32 | 57.68 |
| 130 | 585.72 | 65.04 | 34.96 | 90.56 | 9.44 | 44.06 | 55.94 |
| 140 | 833.76 | 65.51 | 34.49 | 89.61 | 10.39 | 45.96 | 54.04 |

TABLE 7B

| Azeotropic Temperature (° C.) | Azeotropic Pressure (psia) | Vapor-Phase Composition (mass percent) | | Liquid 1 Composition (mass percent) | | Liquid 2 Composition (mass percent) | |
|---|---|---|---|---|---|---|---|
| | | HF | Z-1326mxz | HF | Z-1326mxz | HF | Z-1326mxz |
| −20 | 3.79 | 50.12 | 49.88 | 84.36 | 15.64 | 10.68 | 89.32 |
| −10 | 6.18 | 46.45 | 53.55 | 82.19 | 17.81 | 9.91 | 90.09 |
| 0 | 9.73 | 43.09 | 56.91 | 79.96 | 20.04 | 9.13 | 90.87 |
| 10 | 14.81 | 40.02 | 59.98 | 77.70 | 22.30 | 8.34 | 91.66 |
| 20 | 21.91 | 37.22 | 62.78 | 75.44 | 24.56 | 7.56 | 92.44 |
| 30 | 31.58 | 34.68 | 65.32 | 73.17 | 26.83 | 6.82 | 93.18 |
| 40 | 44.51 | 32.36 | 67.64 | 70.90 | 29.10 | 6.21 | 93.79 |
| 50 | 61.47 | 30.26 | 69.74 | 68.62 | 31.38 | 5.79 | 94.21 |
| 60 | 83.41 | 28.36 | 71.64 | 66.32 | 33.68 | 5.59 | 94.41 |
| 70 | 111.49 | 26.63 | 73.37 | 63.99 | 36.01 | 5.57 | 94.43 |
| 80 | 147.11 | 25.06 | 74.94 | 61.63 | 38.37 | 5.67 | 94.33 |
| 90 | 192.10 | 23.62 | 76.38 | 59.23 | 40.77 | 5.87 | 94.13 |
| 100 | 248.95 | 22.28 | 77.72 | 56.78 | 43.22 | 6.15 | 93.85 |
| 110 | 321.43 | 20.97 | 79.03 | 54.29 | 45.71 | 6.49 | 93.51 |
| 120 | 416.52 | 19.52 | 80.48 | 51.75 | 48.25 | 6.89 | 93.11 |
| 130 | 585.72 | 15.79 | 84.21 | 49.16 | 50.84 | 7.35 | 92.65 |
| 140 | 833.76 | 16.07 | 83.93 | 46.50 | 53.50 | 7.90 | 92.10 |

Example 7. Azeotropic Compositions of Hydrogen Fluoride and 336Mdd (d1-Isomer)

The calculated azeotropic and azeotrope-like ranges for HF/336mdd-d1 mixtures from 0° C. to 140° C. are summarized in Tables 8A-8B.

TABLE 8A

| Azeotropic Temperature (° C.) | Azeotropic Pressure (psia) | Vapor-Phase Composition (mole percent) | | Liquid 1 Composition (mole percent) | | Liquid 2 Composition (mole percent) | |
|---|---|---|---|---|---|---|---|
| | | HF | 336mdd-dl | HF | 336mdd-dl | HF | 336mdd-dl |
| 0 | 7.44 | 97.15 | 2.85 | 98.62 | 1.38 | 48.89 | 51.11 |
| 10 | 11.13 | 96.72 | 3.28 | 98.36 | 1.64 | 45.61 | 54.39 |
| 20 | 16.22 | 96.24 | 3.76 | 98.06 | 1.94 | 42.19 | 57.81 |
| 30 | 23.10 | 95.69 | 4.31 | 97.74 | 2.26 | 39.08 | 60.92 |
| 40 | 32.25 | 95.06 | 4.94 | 97.38 | 2.62 | 36.89 | 63.11 |
| 50 | 44.25 | 94.35 | 5.65 | 96.98 | 3.02 | 35.91 | 64.09 |
| 60 | 59.79 | 93.52 | 6.48 | 96.52 | 3.48 | 35.92 | 64.08 |
| 70 | 79.76 | 92.58 | 7.42 | 96.01 | 3.99 | 36.61 | 63.39 |
| 80 | 105.23 | 91.50 | 8.50 | 95.44 | 4.56 | 37.79 | 62.21 |
| 90 | 137.66 | 90.25 | 9.75 | 94.77 | 5.23 | 39.33 | 60.67 |
| 100 | 179.06 | 88.77 | 11.23 | 94.02 | 5.98 | 41.17 | 58.83 |

TABLE 8A-continued

| Azeotropic Temperature (° C.) | Azeotropic Pressure (psia) | Vapor-Phase Composition (mole percent) | | Liquid 1 Composition (mole percent) | | Liquid 2 Composition (mole percent) | |
|---|---|---|---|---|---|---|---|
| | | HF | 336mdd-dl | HF | 336mdd-dl | HF | 336mdd-dl |
| 110 | 232.63 | 86.90 | 13.10 | 93.14 | 6.86 | 43.29 | 56.71 |
| 120 | 305.32 | 83.97 | 16.03 | 92.10 | 7.90 | 45.69 | 54.31 |
| 130 | 784.86 | 76.77 | 23.23 | 90.87 | 9.13 | 48.39 | 51.61 |
| 140 | 1045.31 | 77.09 | 22.91 | 89.38 | 10.62 | 51.46 | 48.54 |

TABLE 8B

| Azeotropic Temperature (° C.) | Azeotropic Pressure (psia) | Vapor-Phase Composition (mass percent) | | Liquid 1 Composition (mass percent) | | Liquid 2 Composition (mass percent) | |
|---|---|---|---|---|---|---|---|
| | | HF | 336mdd-dl | HF | 336mdd-dl | HF | 336mdd-dl |
| 0 | 7.44 | 74.38 | 25.62 | 85.89 | 14.11 | 7.53 | 92.47 |
| 10 | 11.13 | 71.53 | 28.47 | 83.59 | 16.41 | 6.66 | 93.34 |
| 20 | 16.22 | 68.53 | 31.47 | 81.16 | 18.84 | 5.85 | 94.15 |
| 30 | 23.10 | 65.39 | 34.61 | 78.63 | 21.37 | 5.18 | 94.82 |
| 40 | 32.25 | 62.11 | 37.89 | 75.97 | 24.03 | 4.74 | 95.26 |
| 50 | 44.25 | 58.69 | 41.31 | 73.19 | 26.81 | 4.55 | 95.45 |
| 60 | 59.79 | 55.15 | 44.85 | 70.28 | 29.72 | 4.55 | 95.45 |
| 70 | 79.76 | 51.53 | 48.47 | 67.23 | 32.77 | 4.69 | 95.31 |
| 80 | 105.23 | 47.84 | 52.16 | 64.03 | 35.97 | 4.92 | 95.08 |
| 90 | 137.66 | 44.08 | 55.92 | 60.70 | 39.30 | 5.23 | 94.77 |
| 100 | 179.06 | 40.22 | 59.78 | 57.22 | 42.78 | 5.62 | 94.38 |
| 110 | 232.63 | 36.09 | 63.91 | 53.60 | 46.40 | 6.10 | 93.90 |
| 120 | 305.32 | 30.84 | 69.16 | 49.83 | 50.17 | 6.68 | 93.32 |
| 130 | 784.86 | 21.96 | 78.04 | 45.89 | 54.11 | 7.39 | 92.61 |
| 140 | 1045.31 | 22.27 | 77.73 | 41.74 | 58.26 | 8.28 | 91.72 |

Example 8. Azeotropic Compositions of Hydrogen Fluoride and 336Mdd (Meso-Isomer)

The calculated azeotropic and azeotrope-like ranges for HF/336mdd-meso mixtures from 0° C. to 140° C. are summarized in Tables 9A-9B.

TABLE 9A

| Azeotropic Temperature (° C.) | Azeotropic Pressure (psia) | Vapor-Phase Composition (mole percent) | | Liquid 1 Composition (mole percent) | | Liquid 2 Composition (mole percent) | |
|---|---|---|---|---|---|---|---|
| | | HF | 336mdd-meso | HF | 336mdd-meso | HF | 336mdd-meso |
| 0 | 7.16 | 98.24 | 1.76 | 98.62 | 1.38 | 48.89 | 51.11 |
| 10 | 10.71 | 97.87 | 2.13 | 98.36 | 1.64 | 45.61 | 54.39 |
| 20 | 15.60 | 97.45 | 2.55 | 98.06 | 1.94 | 42.19 | 57.81 |
| 30 | 22.21 | 96.97 | 3.03 | 97.74 | 2.26 | 39.08 | 60.92 |
| 40 | 31.02 | 96.41 | 3.59 | 97.38 | 2.62 | 36.89 | 63.11 |
| 50 | 42.56 | 95.76 | 4.24 | 96.98 | 3.02 | 35.91 | 64.09 |
| 60 | 57.51 | 95.01 | 4.99 | 96.52 | 3.48 | 35.92 | 64.08 |
| 70 | 76.70 | 94.14 | 5.86 | 96.01 | 3.99 | 36.61 | 63.39 |
| 80 | 101.15 | 93.14 | 6.86 | 95.44 | 4.56 | 37.79 | 62.21 |
| 90 | 132.21 | 91.98 | 8.02 | 94.77 | 5.23 | 39.33 | 60.67 |
| 100 | 171.67 | 90.60 | 9.40 | 94.02 | 5.98 | 41.17 | 58.83 |
| 110 | 222.29 | 88.90 | 11.10 | 93.14 | 6.86 | 43.29 | 56.71 |
| 120 | 289.27 | 86.47 | 13.53 | 92.10 | 7.90 | 45.69 | 54.31 |
| 130 | 724.59 | 77.63 | 22.37 | 90.87 | 9.13 | 48.39 | 51.61 |
| 140 | 984.61 | 77.94 | 22.06 | 89.38 | 10.62 | 51.46 | 48.54 |

TABLE 9B

| Azeotropic Temperature (° C.) | Azeotropic Pressure (psia) | Vapor-Phase Composition (mole percent) HF | Vapor-Phase Composition (mole percent) 336mdd-meso | Liquid 1 Composition (mole percent) HF | Liquid 1 Composition (mole percent) 336mdd-meso | Liquid 2 Composition (molepercent) HF | Liquid 2 Composition (molepercent) 336mdd-meso |
|---|---|---|---|---|---|---|---|
| 0 | 7.16 | 82.59 | 17.41 | 85.89 | 14.11 | 7.53 | 92.47 |
| 10 | 10.71 | 79.67 | 20.33 | 83.59 | 16.41 | 6.66 | 93.34 |
| 20 | 15.60 | 76.52 | 23.48 | 81.16 | 18.84 | 5.85 | 94.15 |
| 30 | 22.21 | 73.15 | 26.85 | 78.63 | 21.37 | 5.18 | 94.82 |
| 40 | 31.02 | 69.57 | 30.43 | 75.97 | 24.03 | 4.74 | 95.26 |
| 50 | 42.56 | 65.79 | 34.21 | 73.19 | 26.81 | 4.55 | 95.45 |
| 60 | 57.51 | 61.85 | 38.15 | 70.28 | 29.72 | 4.55 | 95.45 |
| 70 | 76.70 | 57.79 | 42.21 | 67.23 | 32.77 | 4.69 | 95.31 |
| 80 | 101.15 | 53.63 | 46.37 | 64.03 | 35.97 | 4.92 | 95.08 |
| 90 | 132.21 | 49.41 | 50.59 | 60.70 | 39.30 | 5.23 | 94.77 |
| 100 | 171.67 | 45.08 | 54.92 | 57.22 | 42.78 | 5.62 | 94.38 |
| 110 | 222.29 | 40.54 | 59.46 | 53.60 | 46.40 | 6.10 | 93.90 |
| 120 | 289.27 | 35.24 | 64.76 | 49.83 | 50.17 | 6.68 | 93.32 |
| 130 | 724.59 | 22.81 | 77.19 | 45.89 | 54.11 | 7.39 | 92.61 |
| 140 | 984.61 | 23.12 | 76.88 | 41.74 | 58.26 | 8.28 | 91.72 |

Example 9. Azeotropic Compositions of Hydrogen Fluoride and 1317mx

The calculated azeotropic and azeotrope-like ranges for HF/1317mx from −20° C. to 130° C. are summarized in Tables 10A-10B.

TABLE 10A

| Azeotropic Temp (° C.) | Azeotropic Pressure (psia) | Vapor-Phase Composition (mole percent) HF | Vapor-Phase Composition (mole percent) 1317mx | Liquid 1 Composition (mole percent) HF | Liquid 1 Composition (mole percent) 1317mx | Liquid 2 Composition (mole percent) HF | Liquid 2 Composition (mole percent) 1317mx |
|---|---|---|---|---|---|---|---|
| −20 | 4.19 | 89.26 | 10.74 | 99.65 | 0.35 | 1.83 | 98.17 |
| −10 | 6.84 | 88.05 | 11.95 | 99.55 | 0.45 | 2.40 | 97.60 |
| 0 | 10.75 | 86.78 | 13.22 | 99.43 | 0.57 | 3.10 | 96.90 |
| 10 | 16.38 | 85.47 | 14.53 | 99.29 | 0.71 | 3.96 | 96.04 |
| 20 | 24.23 | 84.11 | 15.89 | 99.12 | 0.88 | 4.99 | 95.01 |
| 30 | 34.95 | 82.69 | 17.31 | 98.93 | 1.07 | 6.21 | 93.79 |
| 40 | 49.29 | 81.22 | 18.78 | 98.70 | 1.30 | 7.62 | 92.38 |
| 50 | 68.17 | 79.69 | 20.31 | 98.43 | 1.57 | 9.20 | 90.80 |
| 60 | 92.72 | 78.10 | 21.90 | 98.12 | 1.88 | 10.91 | 89.09 |
| 70 | 124.36 | 76.45 | 23.55 | 97.76 | 2.24 | 12.71 | 87.29 |
| 80 | 164.99 | 74.70 | 25.30 | 97.34 | 2.66 | 14.58 | 85.42 |
| 90 | 217.42 | 72.78 | 27.22 | 96.85 | 3.15 | 16.52 | 83.48 |
| 100 | 286.62 | 70.42 | 29.58 | 96.29 | 3.71 | 18.54 | 81.46 |
| 110 | 449.12 | 62.09 | 37.91 | 95.63 | 4.37 | 20.67 | 79.33 |
| 120 | 647.56 | 63.50 | 36.50 | 94.85 | 5.15 | 22.95 | 77.05 |
| 130 | 851.97 | 64.87 | 35.13 | 93.94 | 6.06 | 25.40 | 74.60 |

TABLE 10B

| Azeotropic Temperature (° C.) | Azeotropic Pressure (psia) | Vapor-Phase Composition (mass percent) HF | Vapor-Phase Composition (mass percent) 1317mx | Liquid 1 Composition (mass percent) HF | Liquid 1 Composition (mass percent) 1317mx | Liquid 2 Composition (mass percent) HF | Liquid 2 Composition (mass percent) 1317mx |
|---|---|---|---|---|---|---|---|
| −20 | 4.19 | 43.44 | 56.56 | 96.34 | 3.66 | 0.17 | 99.83 |
| −10 | 6.84 | 40.50 | 59.50 | 95.34 | 4.66 | 0.23 | 99.77 |
| 0 | 10.75 | 37.76 | 62.24 | 94.18 | 5.82 | 0.29 | 99.71 |
| 10 | 16.38 | 35.22 | 64.78 | 92.82 | 7.18 | 0.38 | 99.62 |
| 20 | 24.23 | 32.84 | 67.16 | 91.27 | 8.73 | 0.48 | 99.52 |
| 30 | 34.95 | 30.62 | 69.38 | 89.50 | 10.50 | 0.61 | 99.39 |
| 40 | 49.29 | 28.55 | 71.45 | 87.51 | 12.49 | 0.76 | 99.24 |
| 50 | 68.17 | 26.61 | 73.39 | 85.29 | 14.71 | 0.93 | 99.07 |
| 60 | 92.72 | 24.79 | 75.21 | 82.83 | 17.17 | 1.12 | 98.88 |
| 70 | 124.36 | 23.08 | 76.92 | 80.13 | 19.87 | 1.33 | 98.67 |
| 80 | 164.99 | 21.44 | 78.56 | 77.18 | 22.82 | 1.55 | 98.45 |
| 90 | 217.42 | 19.81 | 80.19 | 73.99 | 26.01 | 1.80 | 98.20 |
| 100 | 286.62 | 18.03 | 81.97 | 70.56 | 29.44 | 2.06 | 97.94 |
| 110 | 449.12 | 13.15 | 86.85 | 66.90 | 33.10 | 2.35 | 97.65 |
| 120 | 647.56 | 13.85 | 86.15 | 63.00 | 37.00 | 2.68 | 97.32 |
| 130 | 851.97 | 14.58 | 85.42 | 58.89 | 41.11 | 3.05 | 96.95 |

Example 9. Azeotropic Compositions of Hydrogen Fluoride and 337mbf

The calculated azeotropic and azeotrope-like ranges for HF/337mbf from −20° C. to 140° C. are summarized in Tables 11A-11B.

TABLE 11A

| Azeotropic Temp (° C.) | Azeotropic Pressure (psia) | Vapor-Phase Composition (mole percent) HF | Vapor-Phase Composition (mole percent) 337mbf | Liquid 1 Composition (mole percent) HF | Liquid 1 Composition (mole percent) 337mbf | Liquid 2 Composition (mole percent) HF | Liquid 2 Composition (mole percent) 337mbf |
|---|---|---|---|---|---|---|---|
| −20 | 3.32 | 93.92 | 6.08 | 96.84 | 3.16 | 66.34 | 33.66 |
| −10 | 5.38 | 92.63 | 7.37 | 95.85 | 4.15 | 65.99 | 34.01 |
| 0 | 8.42 | 91.22 | 8.78 | 94.63 | 5.37 | 65.64 | 34.36 |
| 10 | 12.77 | 89.68 | 10.32 | 93.13 | 6.87 | 65.25 | 34.75 |
| 20 | 18.83 | 88.04 | 11.96 | 91.31 | 8.69 | 64.80 | 35.20 |
| 30 | 27.06 | 86.31 | 13.69 | 89.09 | 10.91 | 64.34 | 35.66 |
| 40 | 38.02 | 84.52 | 15.48 | 86.35 | 13.65 | 64.05 | 35.95 |
| 50 | 52.34 | 82.69 | 17.31 | 82.76 | 17.24 | 64.53 | 35.47 |
| 60 | 70.75 | 80.95 | 19.05 | 80.95 | 19.05 | — | — |
| 70 | 94.12 | 79.23 | 20.77 | 79.23 | 20.77 | — | — |
| 80 | 123.48 | 77.54 | 22.46 | 77.54 | 22.46 | — | — |
| 90 | 160.11 | 75.85 | 24.15 | 75.85 | 24.15 | — | — |
| 100 | 205.76 | 74.09 | 25.91 | 74.09 | 25.91 | — | — |
| 110 | 263.17 | 72.01 | 27.99 | 72.01 | 27.99 | — | — |
| 120 | 338.96 | 68.23 | 31.77 | 68.23 | 31.77 | — | — |
| 130 | 613.88 | 62.06 | 37.94 | 62.06 | 37.94 | — | — |
| 140 | 791.79 | 62.98 | 37.02 | 62.98 | 37.02 | — | — |

TABLE 11B

| Azeotropic Temperature (° C.) | Azeotropic Pressure (psia) | Vapor-Phase Composition (mass percent) HF | 337mbf | Liquid 1 Composition (mass percent) HF | 337mbf | Liquid 2 Composition (mass percent) HF | 337mbf |
|---|---|---|---|---|---|---|---|
| −20 | 3.32 | 58.56 | 41.44 | 73.71 | 26.29 | 15.29 | 84.71 |
| −10 | 5.38 | 53.52 | 46.48 | 67.90 | 32.10 | 15.09 | 84.91 |
| 0 | 8.42 | 48.75 | 51.25 | 61.74 | 38.26 | 14.89 | 85.11 |
| 10 | 12.77 | 44.32 | 55.68 | 55.40 | 44.60 | 14.67 | 85.33 |
| 20 | 18.83 | 40.26 | 59.74 | 49.03 | 50.97 | 14.43 | 85.57 |
| 30 | 27.06 | 36.60 | 63.40 | 42.78 | 57.22 | 14.18 | 85.82 |
| 40 | 38.02 | 33.33 | 66.67 | 36.67 | 63.33 | 14.03 | 85.97 |
| 50 | 52.34 | 30.42 | 69.58 | 30.53 | 69.47 | 14.28 | 85.72 |
| 60 | 70.75 | 28.01 | 71.99 | 28.01 | 71.99 | — | — |
| 70 | 94.12 | 25.89 | 74.11 | 25.89 | 74.11 | — | — |
| 80 | 123.48 | 24.02 | 75.98 | 24.02 | 75.98 | — | — |
| 90 | 160.11 | 22.34 | 77.66 | 22.34 | 77.66 | — | — |
| 100 | 205.76 | 20.75 | 79.25 | 20.75 | 79.25 | — | — |
| 110 | 263.17 | 19.06 | 80.94 | 19.06 | 80.94 | — | — |
| 120 | 338.96 | 16.44 | 83.56 | 16.44 | 83.56 | — | — |
| 130 | 613.88 | 13.03 | 86.97 | 13.03 | 86.97 | — | — |
| 140 | 791.79 | 13.48 | 86.52 | 13.48 | 86.52 | — | — |

Example 10. Azeotropic Compositions of Hydrogen Fluoride and Z-1325lxz

The calculated azeotropic and azeotrope-like ranges for HF/Z-1325lxz from −20° C. to 140° C. are summarized in Tables 12A-12B.

TABLE 12A

| Azeotropic Temp (° C.) | Azeotropic Pressure (psia) | Vapor-Phase Composition (mole percent) HF | Z-1325lxz | Liquid 1 Composition (mole percent) HF | Z-1325lxz | Liquid 2 Composition (mole percent) HF | Z-1325lxz |
|---|---|---|---|---|---|---|---|
| −20 | 2.97 | 97.78 | 2.22 | 98.17 | 1.83 | 54.26 | 45.74 |
| −10 | 4.76 | 97.25 | 2.75 | 97.86 | 2.14 | 52.19 | 47.81 |
| 0 | 7.38 | 96.66 | 3.34 | 97.54 | 2.46 | 49.92 | 50.08 |
| 10 | 11.12 | 95.98 | 4.02 | 97.19 | 2.81 | 47.44 | 52.56 |
| 20 | 16.32 | 95.24 | 4.76 | 96.82 | 3.18 | 44.79 | 55.21 |
| 30 | 23.40 | 94.43 | 5.57 | 96.44 | 3.56 | 42.08 | 57.92 |
| 40 | 32.88 | 93.54 | 6.46 | 96.03 | 3.97 | 39.64 | 60.36 |
| 50 | 45.34 | 92.59 | 7.41 | 95.59 | 4.41 | 37.89 | 62.11 |
| 60 | 61.49 | 91.58 | 8.42 | 95.13 | 4.87 | 37.01 | 62.99 |
| 70 | 82.19 | 90.52 | 9.48 | 94.63 | 5.37 | 36.91 | 63.09 |
| 80 | 108.42 | 89.42 | 10.58 | 94.10 | 5.90 | 37.38 | 62.62 |
| 90 | 141.40 | 88.29 | 11.71 | 93.51 | 6.49 | 38.24 | 61.76 |
| 100 | 182.63 | 87.12 | 12.88 | 92.87 | 7.13 | 39.39 | 60.61 |
| 110 | 233.98 | 85.92 | 14.08 | 92.18 | 7.82 | 40.76 | 59.24 |
| 120 | 297.98 | 84.66 | 15.34 | 91.41 | 8.59 | 42.32 | 57.68 |
| 130 | 378.28 | 83.29 | 16.71 | 90.56 | 9.44 | 44.06 | 55.94 |
| 140 | 480.98 | 81.64 | 18.36 | 89.61 | 10.39 | 45.96 | 54.04 |

TABLE 12B

| Azeotropic Temperature (° C.) | Azeotropic Pressure (psia) | Vapor-Phase Composition (mass percent) HF | Z-1325lxz | Liquid 1 Composition (mass percent) HF | Z-1325lxz | Liquid 2 Composition (mass percent) HF | Z-1325lxz |
|---|---|---|---|---|---|---|---|
| −20 | 2.97 | 80.40 | 19.60 | 83.28 | 16.72 | 9.94 | 90.06 |
| −10 | 4.76 | 76.72 | 23.28 | 80.99 | 19.01 | 9.22 | 90.78 |
| 0 | 7.38 | 72.90 | 27.10 | 78.65 | 21.35 | 8.49 | 91.51 |
| 10 | 11.12 | 68.99 | 31.01 | 76.29 | 23.71 | 7.75 | 92.25 |
| 20 | 16.32 | 65.07 | 34.93 | 73.93 | 26.07 | 7.02 | 92.98 |
| 30 | 23.40 | 61.20 | 38.80 | 71.58 | 28.42 | 6.33 | 93.67 |
| 40 | 32.88 | 57.42 | 42.58 | 69.23 | 30.77 | 5.76 | 94.24 |
| 50 | 45.34 | 53.78 | 46.22 | 66.88 | 33.12 | 5.37 | 94.63 |

TABLE 12B-continued

| Azeotropic Temperature (° C.) | Azeotropic Pressure (psia) | Vapor-Phase Composition (mass percent) HF | Z-1325lxz | Liquid 1 Composition (mass percent) HF | Z-1325lxz | Liquid 2 Composition (mass percent) HF | Z-1325lxz |
|---|---|---|---|---|---|---|---|
| 60 | 61.49 | 50.32 | 49.68 | 64.52 | 35.48 | 5.19 | 94.81 |
| 70 | 82.19 | 47.07 | 52.93 | 62.14 | 37.86 | 5.16 | 94.84 |
| 80 | 108.42 | 44.03 | 55.97 | 59.73 | 40.27 | 5.26 | 94.74 |
| 90 | 141.40 | 41.23 | 58.77 | 57.29 | 42.71 | 5.45 | 94.55 |
| 100 | 182.63 | 38.64 | 61.36 | 54.82 | 45.18 | 5.70 | 94.30 |
| 110 | 233.98 | 36.23 | 63.77 | 52.31 | 47.69 | 6.02 | 93.98 |
| 120 | 297.98 | 33.94 | 66.06 | 49.76 | 50.24 | 6.39 | 93.61 |
| 130 | 378.28 | 31.69 | 68.31 | 47.17 | 52.83 | 6.83 | 93.17 |
| 140 | 480.98 | 29.27 | 70.73 | 44.53 | 55.47 | 7.34 | 92.66 |

Example 11. Azeotropic Compositions of Hydrogen Fluoride and 1327mz

The calculated azeotropic and azeotrope-like ranges for HF/1327mz (mixture of isomers) from −40° C. to 125° C. are summarized in Tables 13A-13B.

TABLE 13A

| Azeotropic Temperature (° C.) | Azeotropic Pressure (psia) | Vapor-Phase Composition (mole percent) HF | 1327mz | Liquid 1 Composition (mole percent) HF | 1327mz | Liquid 2 Composition (mole percent) HF | 1327mz |
|---|---|---|---|---|---|---|---|
| −40 | 2.31 | 74.51 | 25.49 | 98.70 | 1.30 | 57.92 | 42.08 |
| −30 | 4.13 | 72.84 | 27.16 | 98.45 | 1.55 | 56.16 | 43.84 |
| −20 | 7.02 | 71.27 | 28.73 | 98.17 | 1.83 | 54.26 | 45.74 |
| −10 | 11.38 | 69.79 | 30.21 | 97.86 | 2.14 | 52.19 | 47.81 |
| 0 | 17.71 | 68.40 | 31.60 | 97.54 | 2.46 | 49.92 | 50.08 |
| 10 | 26.61 | 67.09 | 32.91 | 97.19 | 2.81 | 47.44 | 52.56 |
| 20 | 38.76 | 65.86 | 34.14 | 96.82 | 3.18 | 44.79 | 55.21 |
| 30 | 54.98 | 64.70 | 35.30 | 96.44 | 3.56 | 42.08 | 57.92 |
| 40 | 76.20 | 63.59 | 36.41 | 96.03 | 3.97 | 39.64 | 60.36 |

TABLE 13A-continued

| Azeotropic Temperature (° C.) | Azeotropic Pressure (psia) | Vapor-Phase Composition (mole percent) | | Liquid 1 Composition (mole percent) | | Liquid 2 Composition (mole percent) | |
|---|---|---|---|---|---|---|---|
| | | HF | 1327mz | HF | 1327mz | HF | 1327mz |
| 50 | 103.57 | 62.54 | 37.46 | 95.59 | 4.41 | 37.89 | 62.11 |
| 60 | 138.52 | 61.53 | 38.47 | 95.13 | 4.87 | 37.01 | 62.99 |
| 70 | 182.90 | 60.57 | 39.43 | 94.63 | 5.37 | 36.91 | 63.09 |
| 80 | 239.32 | 59.64 | 40.36 | 94.10 | 5.90 | 37.38 | 62.62 |
| 90 | 312.00 | 58.67 | 41.33 | 93.51 | 6.49 | 38.24 | 61.76 |
| 100 | 410.58 | 57.43 | 42.57 | 92.87 | 7.13 | 39.39 | 60.61 |
| 110 | 642.15 | 55.61 | 44.39 | 92.18 | 7.82 | 40.76 | 59.24 |
| 120 | 895.36 | 56.83 | 43.17 | 91.41 | 8.59 | 42.32 | 57.68 |
| 125 | 1041.98 | 57.30 | 42.70 | 91.00 | 9.00 | 43.17 | 56.83 |

TABLE 13B

| Azeotropic Temperature (° C.) | Azeotropic Pressure (psia) | Vapor-Phase Composition (mole percent) | | Liquid 1 Composition (mole percent) | | Liquid 2 Composition (mole percent) | |
|---|---|---|---|---|---|---|---|
| | | HF | 1327mz | HF | 1327mz | HF | HF |
| −40 | 2.31 | 24.31 | 75.69 | 89.33 | 10.67 | 13.14 | 86.86 |
| −30 | 4.13 | 22.77 | 77.23 | 87.45 | 12.55 | 12.34 | 87.66 |
| −20 | 7.02 | 21.42 | 78.58 | 85.47 | 14.53 | 11.53 | 88.47 |
| −10 | 11.38 | 20.25 | 79.75 | 83.42 | 16.58 | 10.71 | 89.29 |
| 0 | 17.71 | 19.22 | 80.78 | 81.31 | 18.69 | 9.87 | 90.13 |
| 10 | 26.61 | 18.31 | 81.69 | 79.17 | 20.83 | 9.03 | 90.97 |
| 20 | 38.76 | 17.49 | 82.51 | 77.01 | 22.99 | 8.18 | 91.82 |
| 30 | 54.98 | 16.76 | 83.24 | 74.84 | 25.16 | 7.39 | 92.61 |
| 40 | 76.20 | 16.10 | 83.90 | 72.65 | 27.35 | 6.73 | 93.27 |
| 50 | 103.57 | 15.50 | 84.50 | 70.46 | 29.54 | 6.28 | 93.72 |
| 60 | 138.52 | 14.95 | 85.05 | 68.23 | 31.77 | 6.07 | 93.93 |
| 70 | 182.90 | 14.45 | 85.55 | 65.96 | 34.04 | 6.04 | 93.96 |
| 80 | 239.32 | 13.97 | 86.03 | 63.65 | 36.35 | 6.16 | 93.84 |
| 90 | 312.00 | 13.50 | 86.50 | 61.30 | 38.70 | 6.37 | 93.63 |
| 100 | 410.58 | 12.91 | 87.09 | 58.89 | 41.11 | 6.67 | 93.33 |
| 110 | 642.15 | 12.10 | 87.90 | 56.43 | 43.57 | 7.03 | 92.97 |
| 120 | 895.36 | 12.64 | 87.36 | 53.91 | 46.09 | 7.46 | 92.54 |
| 125 | 1041.98 | 12.85 | 87.15 | 52.62 | 47.38 | 7.71 | 92.29 |

Example 12. Additional Azeotropic Compositions

Table 14 summarizes a list of additional compounds that form azeotrope and azeotrope-like compositions with hydrogen fluoride that were identified during the synthesis of Z-1336mzz described herein in Scheme 2.

TABLE 14

| Compound ID | Compound Name |
|---|---|
| 114 | 1,2-dichloro-1,1,2,2-tetrafluoroethane |
| 337mde | 2-chloro-1,1,1,3,4,4,4-heptafluorobutane |
| 235da | 2-chloro-1,1,1,3,3-pentafluoropropane |
| 123a | 1,2-dichloro-1,1,2-trifluoroethane |
| 336maf | 2,2-dichloro-1,1,1,4,4,4-hexafluorobutane |
| 336lbf | 1,2-dichloro-1,1,2,4,4,4-hexafluorobutane |
| 1325dx | Z & E-1,2-dichloro-3,3,4,4,4-pentafluorobut-1-ene |
| 234da | 2,3-dichloro-1,1,1,3-tetrafluoropropane |
| 335ldd | 1,2,3-trichloro-1,1,4,4,4-pentafluorobutane |
| 122 | 1,2,2-trichloro-1,1-difluoroethane |
| 112 | 1,1,2,2-tetrachloro-1,2-difluoroethane |
| 112a | 1,1,1,2-tetrachloro-2,2-difluoroethane |
| 1314 | 1,2-dichloro-3,3,4,4-tetrafluorocyclobut-1-ene |
| 1323azd | 1,1,2,3-tetrachloro-4,4,4-trifluorobut-1-ene |

Other Embodiments

1. In some embodiments, the present application provides a composition, comprising:
i) hydrogen fluoride; and
ii) a compound of Formula I:

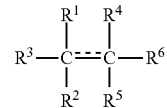

wherein ===== refers to a single bond or a double bond;
$R^1$ is selected from the group consisting of H, halo, and $C_{1-3}$ haloalkyl;
$R^2$ is selected from the group consisting of halo and $C_{1-3}$ haloalkyl;
$R^3$ is selected from the group consisting of $C_{1-3}$ haloalkyl; or alternatively, $R^3$ is absent when ===== forms a double bond;
$R^4$ is selected from the group consisting of halo and $C_{1-3}$ haloalkyl;
$R^5$ is selected from the group consisting of H, $C_{1-3}$ haloalkyl and $C_{1-3}$ haloalkenyl, wherein $R^5$ is not H when ===== forms a double bond;
$R^6$ is H;
or alternatively, $R^6$ is absent when ===== forms a double bond;
wherein when ===== forms a single bond and $R^5$ is H, then $R^1$ is chloro, $R^2$ is fluoro, and $R^3$ and $R^4$ are each trifluoromethyl; and
wherein the compound of Formula I is present in an amount effective to form an azeotrope composition or an azeotrope-like composition with the hydrogen fluoride.

2. The composition of embodiment 1, wherein $R^1$ is H or halo.

3. The composition of embodiment 1, wherein $R^1$ is selected from the group consisting of H, chloro, and fluoro.

4. The composition of any one of embodiments 1 to 3, wherein $R^2$ is selected from the group consisting of chloro and $C_{1-3}$ fluoroalkyl.

5. The composition of any one of embodiments 1 to 3, wherein $R^2$ is selected from the group consisting of chloro, fluoro, and trifluoromethyl.

6. The composition of any one of embodiments 1 to 5, wherein $R^4$ is halo.

7. The composition of any one of embodiments 1 to 5, wherein $R^4$ is chloro or fluoro.

8. The composition of any one of embodiments 1 to 7, wherein $R^5$ is H, $C_{1-3}$ fluoroalkyl or $C_{1-3}$ chloroalkenyl.

9. The composition of any one of embodiments 1 to 7, wherein $R^5$ is trifluoromethyl or 1,2,2-trichloroethenyl.

10. The composition of any one of embodiments 1 to 9, wherein ===== is a single bond.

11. The composition of any one of embodiments 1 to 10, wherein $R^3$ is H.

12. The composition of any one of embodiments 1 to 11, wherein $R^6$ is H.

13. The composition of any one of embodiments 1 to 9, wherein ===== is a double bond.

14. The composition of embodiment 1, wherein the compound of Formula I is selected from the group consisting of:
2,3-dichlorohexafluoro-2-butene;
(E)-2,3-dichlorohexafluoro-2-butene;

(Z)-2,3-dichlorohexafluoro-2-butene;
(E)-2-chloro-1,1,1,4,4,4-hexafluoro-2-butene;
(Z)-2-chloro-1,1,1,4,4,4-hexafluoro-2-butene;
dl-2,3-dichloro-1,1,1,4,4,4-hexafluorobutane;
meso-2,3-dichloro-1,1,1,4,4,4-hexafluorobutane;
2-chloro-1,1,1,3,4,4,4-heptafluorobut-2-ene;
2-chloro-1,1,1,2,4,4,4-heptafluorobutane;
(Z)-1,2-dichloro-1,1,4,4,4-pentafluorobut-2-ene; and
1,1,1,2,4,4,4-heptafluorobut-2-ene;

wherein the compound of Formula I is present in an amount effective to form an azeotrope or an azeotrope-like composition with the hydrogen fluoride.

15. The composition of embodiment 1, wherein the compound of Formula I is (E)-2,3-dichlorohexafluoro-2-butene, wherein the (E)-2,3-dichlorohexafluoro-2-butene is present in an amount effective to form an azeotrope or an azeotrope-like composition with the hydrogen fluoride.

16. The composition of embodiment 15, wherein the composition comprises from about 75 to about 99 mole percent hydrogen fluoride and from about 25 to about 1 mole percent (E)-2,3-dichlorohexafluoro-2-butene.

17. The composition of embodiment 15 or 16, wherein the composition has a boiling point of from about 0° C. to about 130° C. at a pressure of from about 5 psia to about 1000 psia.

18. The composition of embodiment 1, wherein the compound of Formula I is (Z)-2,3-dichlorohexafluoro-2-butene, wherein the (Z)-2,3-dichlorohexafluoro-2-butene is present in an amount effective to form an azeotrope or an azeotrope-like composition with the hydrogen fluoride.

19. The composition of embodiment 18, wherein the composition comprises from about 75 to about 99 mole percent hydrogen fluoride and from about 25 to about 1 mole percent (Z)-2,3-dichlorohexafluoro-2-butene.

20. The composition of embodiment 18 or 19, wherein the composition has a boiling point of from about 0° C. to about 130° C. at a pressure of from about 5 psia to about 1000 psia.

21. The composition of embodiment 1, wherein the compound of Formula I is a mixture of (E)-2,3-dichlorohexafluoro-2-butene and (Z)-2,3-dichlorohexafluoro-2-butene isomers, wherein the mixture of 2,3-dichlorohexafluoro-2-butene are present in an amount effective to form an azeotrope or an azeotrope-like composition with the hydrogen fluoride.

22. The composition of embodiment 21, wherein the composition from about 75 to about 99 mole percent hydrogen fluoride and from about 25 to about 1 mole percent of the mixture of (E)-2,3-dichlorohexafluoro-2-butene and (Z)-2,3-dichlorohexafluoro-2-butene isomers.

23. The composition of embodiment 21 or 22, wherein the composition has a boiling point of from about 0° C. to about 130° C. at a pressure of from about 5 psia to about 1100 psia.

24. The composition of embodiment 1, wherein the compound of Formula I is (E)-2-chloro-1,1,1,4,4,4-hexafluoro-2-butene, wherein the (E)-2-chloro-1,1,1,4,4,4-hexafluoro-2-butene is present in an amount effective to form an azeotrope or an azeotrope-like composition with the hydrogen fluoride.

25. The composition of embodiment 24, wherein the composition comprises from about 60 to about 99 mole percent hydrogen fluoride and from about 40 to about 1 mole percent (E)-2-chloro-1,1,1,4,4,4-hexafluoro-2-butene.

26. The composition of embodiment 24 or 25, wherein the composition has a boiling point of from about −25° C. to about 145° C. at a pressure of from about 1 psia to about 800 psia.

27. The composition of embodiment 1, wherein the compound of Formula I is (Z)-2-chloro-1,1,1,4,4,4-hexafluoro-2-butene, wherein the (Z)-2-chloro-1,1,1,4,4,4-hexafluoro-2-butene is present in an amount effective to form an azeotrope or an azeotrope-like composition with the hydrogen fluoride.

28. The composition of embodiment 27, wherein the composition comprises from about 65 to about 95 mole percent hydrogen fluoride and from about 35 to about 5 mole percent (Z)-2-chloro-1,1,1,4,4,4-hexafluoro-2-butene.

29. The composition of embodiment 27 or 28, wherein the composition has a boiling point of from about −25° C. to about 145° C. at a pressure of from about 1 psia to about 850 psia.

30. The composition of embodiment 1, wherein the compound of Formula I is 2,3-dichloro-1,1,1,4,4,4-hexafluorobutane, wherein the 2,3-dichloro-1,1,1,4,4,4-hexafluorobutane is present in an amount effective to form an azeotrope or an azeotrope-like composition with the hydrogen fluoride.

31. The composition of embodiment 30, wherein the 2,3-dichloro-1,1,1,4,4,4-hexafluorobutane is dl-2,3-dichloro-1,1,1,4,4,4-hexafluorobutane.

32. The composition of embodiment 31, wherein the composition comprises from about 75 to about 99 mole percent hydrogen fluoride and from about 25 to about 1 mole percent dl-2,3-dichloro-1,1,1,4,4,4-hexafluorobutane.

33. The composition of embodiment 31 or 32, wherein the composition has a boiling point of from about 0° C. to about 140° C. at a pressure of from about 5 psia to about 1000 psia.

34. The composition of embodiment 30, wherein the 2,3-dichloro-1,1,1,4,4,4-hexafluorobutane is meso-2,3-dichloro-1,1,1,4,4,4-hexafluorobutane.

35. The composition of embodiment 34, wherein the composition comprises from about 75 to about 99 mole percent hydrogen fluoride and from about 25 to about 1 mole percent meso-2,3-dichloro-1,1,1,4,4,4-hexafluorobutane.

36. The composition of embodiment 34 or 35, wherein the composition has a boiling point of from about 0° C. to about 140° C. at a pressure of from about 5 psia to about 1000 psia.

37. The composition of embodiment 1, wherein the compound of Formula I is 2-chloro-1,1,1,3,4,4,4-heptafluorobut-2-ene, wherein the 2-chloro-1,1,1,3,4,4,4-heptafluorobut-2-ene is present in an amount effective to form an azeotrope or an azeotrope-like composition with the hydrogen fluoride.

38. The composition of embodiment 37, wherein the composition comprises from about 60 to about 90 mole percent hydrogen fluoride and from about 40 to about 10 mole percent 2-chloro-1,1,1,3,4,4,4-heptafluorobut-2-ene.

39. The composition of embodiment 37 or 38, wherein the composition has a boiling point of from about −25° C. to about 145° C. at a pressure of from about 1 psia to about 850 psia.

40. The composition of embodiment 1, wherein the compound of Formula I is 2-chloro-1,1,1,2,4,4,4-heptafluorobutane, wherein the 2-chloro-1,1,1,2,4,4,4-heptafluorobutane is present in an amount effective to form an azeotrope or an azeotrope-like composition with the hydrogen fluoride.

41. The composition of embodiment 40, wherein the composition comprises from about 60 to about 95 mole percent hydrogen fluoride and from about 40 to about 5 mole percent 2-chloro-1,1,1,2,4,4,4-heptafluorobutane.

42. The composition of embodiment 40 or 41, wherein the composition has a boiling point of from about −25° C. to about 145° C. at a pressure of from about 1 psia to about 800 psia.

43. The composition of embodiment 1, wherein the compound of Formula I is (Z)-1,2-dichloro-1,1,4,4,4-pentafluorobut-2-ene, wherein the (Z)-1,2-dichloro-1,1,4,4,4-pentafluorobut-2-ene is present in an amount effective to form an azeotrope or an azeotrope-like composition with the hydrogen fluoride.

44. The composition of embodiment 43, wherein the composition comprises from about 80 to about 99 mole percent hydrogen fluoride and from about 20 to about 1 mole percent (Z)-1,2-dichloro-1,1,4,4,4-pentafluorobut-2-ene.

45. The composition of embodiment 43 or 44, wherein the composition has a boiling point of from about −25° C. to about 145° C. at a pressure of from about 1 psia to about 500 psia.

46. The composition of embodiment 1, wherein the compound of Formula I is 1,1,1,2,4,4,4-heptafluorobut-2-ene, wherein the 1,1,1,2,4,4,4-heptafluorobut-2-ene is present in an amount effective to form an azeotrope or an azeotrope-like composition with the hydrogen fluoride.

47. The composition of embodiment 46, wherein the composition comprises from about 55 to about 75 mole percent hydrogen fluoride and from about 45 to about 25 mole percent 1,1,1,2,4,4,4-heptafluorobut-2-ene.

48. The composition of embodiment 46 or 47, wherein the composition has a boiling point of from about −40° C. to about 125° C. at a pressure of from about 1 psia to about 1000 psia.

49. The composition of embodiment 1, wherein the composition comprises:

from about 75 to about 99 mole percent hydrogen fluoride and from about 25 to about 1 mole percent (E)-2,3-dichlorohexafluoro-2-butene, wherein the composition has a boiling point of from about 0° C. to about 130° C. at a pressure of from about 5 psia to about 1000 psia; or from about 75 to about 99 mole percent hydrogen fluoride and from about 25 to about 1 mole percent (Z)-2,3-dichlorohexafluoro-2-butene, wherein the composition has a boiling point of from about 0° C. to about 130° C. at a pressure of from about 5 psia to about 1000 psia; or from about 75 to about 99 mole percent hydrogen fluoride and from about 25 to about 1 mole percent 2,3-dichlorohexafluoro-2-butene, wherein the composition has a boiling point of from about 0° C. to about 130° C. at a pressure of from about 5 psia to about 1100 psia; or from about 60 to about 99 mole percent hydrogen fluoride and from about 40 to about 1 mole percent (E)-2-chloro-1,1,1,4,4,4-hexafluoro-2-butene, wherein the composition has a boiling point of from about −25° C. to about 145° C. at a pressure of from about 1 psia to about 800 psia; or from about 60 to about 95 mole percent hydrogen fluoride and from about 40 to about 5 mole percent (Z)-2-chloro-1,1,1,4,4,4-hexafluoro-2-butene, wherein the composition has a boiling point of from about −25° C. to about 145° C. at a pressure of from about 1 psia to about 850 psia; or from about 75 to about 99 mole percent hydrogen fluoride and from about 25 to about 1 mole percent d1-2,3-dichloro-1,1,1,4,4,4-hexafluorobutane, wherein the composition has a boiling point of from about 0° C. to about 140° C. at a pressure of from about 5 psia to about 1000 psia; or from about 75 to about 99 mole percent hydrogen fluoride and from about 25 to about 1 mole percent meso-2,3-dichloro-1,1,1,4,4,4-hexafluorobutane, wherein the composition has a boiling point of from about 0° C. to about 140° C. at a pressure of from about 5 psia to about 1000 psia; or from about 60 to about 90 mole percent hydrogen fluoride and from about 40 to about 10 mole percent 2-chloro-1,1,1,3,4,4,4-heptafluorobut-2-ene, wherein the composition has a boiling point of from about −25° C. to about 145° C. at a pressure of from about 1 psia to about 850 psia; or from about 60 to about 95 mole percent hydrogen fluoride and from about 40 to about 5 mole percent 2-chloro-1,1,1,2,4,4,4-heptafluorobutane, wherein the composition has a boiling point of from about −25° C. to about 145° C. at a pressure of from about 1 psia to about 800 psia; or from about 80 to about 99 mole percent hydrogen fluoride and from about 20 to about 1 mole percent (Z)-1,2-dichloro-1,1,4,4,4-pentafluorobut-2-ene, wherein the composition has a boiling point of from about −25° C. to about 145° C. at a pressure of from about 1 psia to about 500 psia; or from about 55 to about 75 mole percent hydrogen fluoride and from about 45 to about 25 mole percent 1,1,1,2,4,4,4-heptafluorobut-2-ene, wherein the composition has a boiling point of from about −40° C. to about 125° C. at a pressure of from about 1 psia to about 1000 psia.

50. In some embodiments, the present application further provides a composition, comprising:
  i) hydrogen fluoride; and
  ii) a compound selected from the group consisting of:
    2,3-dichlorohexafluoro-2-butene;
    2-chloro-1,1,1,4,4,4-hexafluoro-2-butene;
    2,3-dichloro-1,1,1,4,4,4-hexafluorobutane;
    2-chloro-1,1,1,3,4,4,4-heptafluorobut-2-ene;
    1,1,1,2,4,4,4-heptafluorobut-2-ene;
    2-chloro-1,1,1,2,4,4,4-heptafluorobutane;
    1,2-dichloro-1,1,4,4,4-pentafluorobut-2-ene;
    1,2-dichloro-1,1,2,2-tetrafluoroethane;
    2-chloro-1,1,1,3,4,4,4-heptafluorobutane;
    2-chloro-1,1,1,3,3-pentafluoropropane;
    1,2-dichloro-1,1,2-trifluoroethane;
    2,2-dichloro-1,1,1,4,4,4-hexafluorobutane;
    1,2-dichloro-1,1,2,4,4,4-hexafluorobutane;
    1,2-dichloro-3,3,4,4,4-pentafluorobut-1-ene;
    2,3-dichloro-1,1,1,3-tetrafluoropropane;
    1,2,3-trichloro-1,1,4,4,4-pentafluorobutane;
    1,2,2-trichloro-1,1-difluoroethane;
    1,1,2,2-tetrachloro-1,2-difluoroethane;
    1,1,1,2-tetrachloro-2,2-difluoroethane;
    1,2-dichloro-3,3,4,4-tetrafluorocyclobut-1-ene; and
    1,1,2,3-tetrachloro-4,4,4-trifluorobut-1-ene;
  wherein the compound is present in an amount effective to form an azeotrope composition or an azeotrope-like composition with the hydrogen fluoride.

51. In some embodiments, the present application further provides a composition, comprising:
  i) hydrogen fluoride; and
  ii) a compound selected from the group consisting of:
    2,3-dichlorohexafluoro-2-butene;
    (E)-2,3-dichlorohexafluoro-2-butene;
    (Z)-2,3-dichlorohexafluoro-2-butene;
    (E)-2-chloro-1,1,1,4,4,4-hexafluoro-2-butene;
    (Z)-2-chloro-1,1,1,4,4,4-hexafluoro-2-butene;
    (d1)-2,3-dichloro-1,1,1,4,4,4-hexafluorobutane;
    meso-2,3-dichloro-1,1,1,4,4,4-hexafluorobutane;
    2-chloro-1,1,1,3,4,4,4-heptafluorobut-2-ene;
    1,1,1,2,4,4,4-heptafluorobut-2-ene;
    2-chloro-1,1,1,2,4,4,4-heptafluorobutane;
    (Z)-1,2-dichloro-1,1,4,4,4-pentafluorobut-2-ene;
    1,2-dichloro-1,1,2,2-tetrafluoroethane;
    2-chloro-1,1,1,3,4,4,4-heptafluorobutane;
    2-chloro-1,1,1,3,3-pentafluoropropane;
    1,2-dichloro-1,1,2-trifluoroethane;
    2,2-dichloro-1,1,1,4,4,4-hexafluorobutane;
    1,2-dichloro-1,1,2,4,4,4-hexafluorobutane;
    1,2-dichloro-3,3,4,4,4-pentafluorobut-1-ene;
    2,3-dichloro-1,1,1,3-tetrafluoropropane;
    1,2,3-trichloro-1,1,4,4,4-pentafluorobutane;

1,2,2-trichloro-1,1-difluoroethane;
1,1,2,2-tetrachloro-1,2-difluoroethane;
1,1,1,2-tetrachloro-2,2-difluoroethane;
1,2-dichloro-3,3,4,4-tetrafluorocyclobut-1-ene; and
1,1,2,3-tetrachloro-4,4,4-trifluorobut-1-ene;
wherein the compound is present in an amount effective to form an azeotrope composition or an azeotrope-like composition with the hydrogen fluoride.

52. The composition of any one of embodiments 1 to 51, wherein the azeotrope or azeotrope-like composition is a heterogeneous azeotrope composition or heterogeneous azeotrope-like composition.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

What is claimed is:

1. A composition comprising:
   a) hydrogen fluoride; and
   b) a compound selected from the group consisting of:
      (E)-2-chloro-1,1,1,4,4,4-hexafluoro-2-butene; and
      (Z)-2-chloro-1,1,1,4,4,4-hexafluoro-2-butene;
   wherein the compound is present in an amount effective to form an azeotrope or an azeotrope-like composition with the hydrogen fluoride.

2. The composition of claim 1, wherein the compound is (E)-2-chloro-1,1,1,4,4,4-hexafluoro-2-butene, wherein the (E)-2-chloro-1,1,1,4,4,4-hexafluoro-2-butene is present in an amount effective to form an azeotrope or an azeotrope-like composition with the hydrogen fluoride.

3. The composition of claim 1, wherein the composition has a boiling point of from about −25° C. to about 145° C. at a pressure of from about 1 psia to about 800 psia.

4. The composition of claim 1, wherein the compound is (Z)-2-chloro-1,1,1,4,4,4-hexafluoro-2-butene, wherein the (Z)-2-chloro-1,1,1,4,4,4-hexafluoro-2-butene is present in an amount effective to form an azeotrope or an azeotrope-like composition with the hydrogen fluoride.

5. The composition of claim 4, wherein the composition has a boiling point of from about −25° C. to about 145° C. at a pressure of from about 1 psia to about 850 psia.

* * * * *